(12) United States Patent
Dimarchi et al.

(10) Patent No.: US 9,309,301 B2
(45) Date of Patent: Apr. 12, 2016

(54) GLUCAGON/GLP-1 RECEPTOR CO-AGONISTS

(75) Inventors: Richard D. Dimarchi, Carmel, IN (US); David L. Smiley, Bloomington, IN (US); Bin S. Yang, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 65 days.

(21) Appl. No.: 14/127,469

(22) PCT Filed: Jun. 12, 2012

(86) PCT No.: PCT/US2012/042085
§ 371 (c)(1),
(2), (4) Date: Mar. 24, 2014

(87) PCT Pub. No.: WO2012/177444
PCT Pub. Date: Dec. 27, 2012

(65) Prior Publication Data
US 2014/0206607 A1    Jul. 24, 2014

Related U.S. Application Data

(60) Provisional application No. 61/500,025, filed on Jun. 22, 2011.

(51) Int. Cl.
| | | |
|---|---|---|
| A61K 38/26 | (2006.01) | |
| C07K 14/605 | (2006.01) | |
| A61K 47/48 | (2006.01) | |
| G01N 33/74 | (2006.01) | |
| A61K 38/00 | (2006.01) | |

(52) U.S. Cl.
CPC .......... *C07K 14/605* (2013.01); *A61K 47/48215* (2013.01); *G01N 33/74* (2013.01); *A61K 38/00* (2013.01); *C07K 2319/00* (2013.01); *G01N 2333/605* (2013.01); *G01N 2800/042* (2013.01); *G01N 2800/085* (2013.01); *G01N 2800/2821* (2013.01); *G01N 2800/2835* (2013.01)

(58) Field of Classification Search
CPC .................. A61K 38/26; A61K 47/48215
See application file for complete search history.

(56) References Cited

U.S. PATENT DOCUMENTS

| | | | |
|---|---|---|---|
| 4,275,152 A | 6/1981 | Esders et al. | |
| 5,359,030 A | 10/1994 | Ekwuribe | |
| 5,510,459 A | 4/1996 | Smith et al. | |
| 5,512,549 A | 4/1996 | Chen et al. | |
| 5,545,618 A | 8/1996 | Buckley et al. | |
| 5,665,705 A | 9/1997 | Merrifield et al. | |
| 5,783,674 A | 7/1998 | Geysin et al. | |
| 6,191,102 B1 | 2/2001 | DiMarchi et al. | |
| 6,329,336 B1 | 12/2001 | Bridon et al. | |
| 6,583,111 B1 | 6/2003 | DiMarchi et al. | |
| 6,677,136 B2 | 1/2004 | Marshall et al. | |
| 7,192,922 B2 | 3/2007 | Shannon et al. | |
| 7,211,557 B2 | 5/2007 | DiMarchie et al. | |
| 7,326,688 B2 | 2/2008 | O'Harte et al. | |
| 7,557,183 B2 | 7/2009 | DiMarchi et al. | |
| 7,576,059 B2 | 8/2009 | Jonassen et al. | |
| 8,053,560 B2 | 11/2011 | Sheffer et al. | |
| 2002/0049164 A1 | 4/2002 | Demuth et al. | |
| 2003/0021795 A1 | 1/2003 | Houston et al. | |
| 2003/0143183 A1 | 7/2003 | Knudsen et al. | |
| 2003/0195157 A1 | 10/2003 | Natarajan et al. | |
| 2003/0204063 A1 | 10/2003 | Gravel et al. | |
| 2004/0002468 A1 | 1/2004 | Wadsworth et al. | |
| 2004/0235710 A1 | 11/2004 | DeFelippis et al. | |
| 2005/0070469 A1 | 3/2005 | Bloom et al. | |
| 2005/0095679 A1 | 5/2005 | Prescott et al. | |
| 2005/0124550 A1 | 6/2005 | Peri | |
| 2005/0153890 A1 | 7/2005 | Pan et al. | |
| 2005/0288248 A1 | 12/2005 | Pan et al. | |
| 2006/0003417 A1 | 1/2006 | Pan et al. | |
| 2006/0003935 A1 | 1/2006 | Pan et al. | |
| 2006/0084604 A1 | 4/2006 | Kitaura et al. | |
| 2006/0171920 A1 | 8/2006 | Shechter et al. | |
| 2006/0210534 A1 | 9/2006 | Lee et al. | |
| 2006/0252916 A1 | 11/2006 | DiMarchi et al. | |
| 2006/0286129 A1 | 12/2006 | Sarubbi | |
| 2007/0042956 A1 | 2/2007 | Johansen et al. | |
| 2007/0173452 A1 | 7/2007 | DiMarchi et al. | |
| 2007/0203058 A1 | 8/2007 | Lau et al. | |
| 2007/0287670 A1 | 12/2007 | Natarajan et al. | |
| 2008/0113905 A1 | 5/2008 | DiMarchi et al. | |
| 2008/0125574 A1 | 5/2008 | Sheffer et al. | |
| 2008/0312157 A1 | 12/2008 | Levy et al. | |
| 2008/0318837 A1 | 12/2008 | Quay et al. | |

(Continued)

FOREIGN PATENT DOCUMENTS

| | | |
|---|---|---|
| CA | 2024855 | 3/1992 |
| EP | 0220958 | 5/1987 |

(Continued)

OTHER PUBLICATIONS

Carrington et al., "Human Oxyntomodulin Analog Peptide," XP-002732869, Oct. 14, 2010, Database GenSeq.

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

Ahn, J.M. et al., A new approach to search for the bioactive conformation of glucagon: positional cyclization scanning, *J. Med. Chem.*, 44(19): 3109-16, Sep. 13, 2001.

Ahn, J.M. et al., Development of potent truncated glucagon antagonists, *J. Med. Chem.*, 44(9): 1372-9, Apr. 26, 2001. (Abstract).

Chabenne et al., Optimization of the native glucagon sequence for medicinal purposes, J. Diabetes. Sci. Technol., 4(6): 1322-31, Nov. 1, 2010.

(Continued)

*Primary Examiner* — Gyan Chandra
(74) *Attorney, Agent, or Firm* — Barnes & Thornburg LLP

(57) ABSTRACT

Provided herein are peptides and variant peptides that exhibit enhanced activity at the GLP-1 receptor, as compared to native glucagon.

24 Claims, 1 Drawing Sheet

(56) References Cited

U.S. PATENT DOCUMENTS

| | | |
|---|---|---|
| 2009/0036364 A1 | 2/2009 | Levy et al. |
| 2009/0054305 A1 | 2/2009 | Schlein et al. |
| 2009/0062192 A1 | 3/2009 | Christensen et al. |
| 2009/0074769 A1 | 3/2009 | Glaesner et al. |
| 2009/0137456 A1 | 5/2009 | DiMarchi et al. |
| 2009/0186817 A1 | 7/2009 | Ghosh et al. |
| 2009/0192072 A1 | 7/2009 | Pillutla et al. |
| 2010/0190699 A1 | 7/2010 | DiMarchi et al. |
| 2010/0190701 A1 | 7/2010 | Day et al. |
| 2010/0204105 A1 | 8/2010 | Riber et al. |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| EP | 0479210 | 4/1992 |
| EP | 0708179 | 4/1996 |
| EP | 0815135 | 9/1996 |
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| JP | 2003/192698 | 7/2003 |
| WO | WO91/11457 | 8/1991 |
| WO | WO96/29342 | 9/1996 |
| WO | WO 9707814 | 3/1997 |
| WO | 97/29180 | 8/1997 |
| WO | WO9746584 | 12/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO99/67278 | 12/1999 |
| WO | WO 0020592 | 4/2000 |
| WO | 00/34331 | 6/2000 |
| WO | WO00/42026 | 7/2000 |
| WO | WO 0058360 | 10/2000 |
| WO | 01/83527 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO03/058203 | 7/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO2004000354 | 12/2003 |
| WO | 2004/022004 | 3/2004 |
| WO | 2004/067548 | 8/2004 |
| WO | WO 2004078777 | 9/2004 |
| WO | 2004/093823 | 11/2004 |
| WO | 2004/105781 | 12/2004 |
| WO | 2004/105790 | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | WO2007/124461 | 1/2007 |
| WO | 2007/022123 | 2/2007 |
| WO | WO 2007028632 | 3/2007 |
| WO | WO2007028633 | 3/2007 |
| WO | 2007/056362 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | 2009/059278 | 5/2009 |
| WO | 2009/095479 | 8/2009 |
| WO | 2009/099763 | 8/2009 |
| WO | 2009/155257 | 12/2009 |
| WO | 2009/155258 A2 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |
| WO | 2011/094337 | 8/2011 |
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.

GenBank entry AAH05278. Jul. 15, 2006. [Retrieved from the Internet Jun. 18, 2009: ~http://www._ncbi._nim.n_ih.gov/protein/13528972>].

Habegger et al., The metabolic actions of glucagon revisited, *Nat. Rev. Endocrinol.*, 6(12): 689-97, Oct. 19, 2010.

Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.

Heppner et al., Glucagon regulation of energy metabolism, *Physiol Behav.*, 100(5): 545-8, Apr. 8, 2010.

Hruby et al., "The Design and Biological Activities of Glucagon Agonists and Antagonists, and Their Use in Examining the Mechanisms of Glucose Action," *Curr. Med. Chem.-Imm., Endoc. & Metab. Agents*, 2001, 1, pp. 199-215.

Joshi et al, "Studies on the Mechanism of Aspartic Acid Cleavage and Glutamine Deamidation in the Acidic Degradation of Glucagon," *Journal of Pharmaceutical Sciences*, vol. 94, No. 9, Sep. 2005, pp. 1912-1927.

Joshi et al., "The Degradation Pathways of Glucagon in Acidic Solutions," *International Journal of Pharmaceutics*, 203 (2000), pp. 115-125.

Joshi et al., "The Estimation of Glutaminyl Deamidation and Aspartyl Cleavage Rates in Glucagon," *International Journal of Pharmaceutics*, 273 (2004), pp. 213-219.

Krstenansky et al., "Importance of the C-terminal α-helical structure for glucagon's biological activity," Int. J. Peptide Protein Res., 32, 1988, 468-475.

(56) References Cited

OTHER PUBLICATIONS

Lee et al., "Synthesis, Characterization, and Pharmacokinetic Studies of PEGylated Glucagon-like Peptide-1," *Bioconjugate Chem.*, 2005, vol. 16, No. 2, pp. 377-382.

Levy et al., Optimization of the C-terminal Sequence in Glucagon to Maximize Receptor Affinity, Poster Presentation, Jun. 19, 2005.

Levy et al., Optimization of the C-terminal Sequence in Glucagon to Maximize Receptor Affinity, *Understanding Biology Using Peptides*, American Peptide Society, Apr. 2006.

Li et al., Crystallization and preliminary X-ray analysis of anti-obesity peptide hormone oxyntomodulin, *Protein & Peptide Letters*, 15(2): 232-4 (2008).

Li et al., Design, synthesis and crystallization of a novel glucagon analog as a therapeutic agent, *Acta Crystallogr. Sect. F Struct. Biol. Cryst. Commun.*, 63(Pt 7):599-601, Jun. 15, 2007.

Li et al., Structural Basis for Enhanced Solublity of a C-Terminally Extended Glucagon Analog, *Biopolymers.*, 96(4): 480 (2011).

M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.

McKee et al., Receptor Binding and Adenylate Cyclase Activities of Glucagon Analogues Modified in the N-Terminal Region, Biochemistry, 25: 1650-6 (1986).

Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.

Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.

Pan et al., Design of a Long Acting Peptide Functioning as Both a Glucagon-like Peptide-1 Receptor Agonist and a Glucagon Receptor Agonist, *J. Biol. Chem.*, 281(18): 12506-15, Table 1, May 5, 2006.

Patterson et al., A novel human-based receptor antagonist of sustained action reveals body weight control by endogenous GLP-1, *ACS Chem Biol.*, 6(2): 135-45 Nov. 4, 2010.

PCT International Search Report for PCT/US2008/050099 completed by the US Searching Authority on Sep. 1, 2008.

PCT International Search Report for PCT/US2008/053857 completed by the US Searching Authority on Sep. 16, 2008.

PCT International Search Report for PCT/US2008/080973 completed by the US Searching Authority on Jun. 6, 2009.

PCT International Search Report for PCT/US2008/081333 completed by the US Searching Authority on Mar. 12, 2009.

PCT International Search Report for PCT/US2009/031593 completed by the US Searching Authority on Jun. 18, 2009.

Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.

Sapse et al., The Role of Sale Bridge Formation in Glucagon: An Experimental and Theoretical Study of Glucagon Analogs and Peptide Fragments of Glucagon, *Molec. Med.*, 8(5): 251-62, May 1, 2002.

Stigsnaes et al., "Characterisation and Physical Stability of PEGylated Glucagon," *International Journal of Pharmaceutics*, 330 (2007), pp. 87-98.

Traylor et al., Identification of the High Potency Glucagon Agonist with Enhanced Biophysical Stability and Aqueous Solubility, Poster Abstract PY 10, pp. 505-506, Jun. 10, 2005.

Trivedi, D. et al., Design and synthesis of conformationally constrained glucagon analogues, *J. Med. Chem.*, 43(9): 1714-22, May 4, 2000 (Abstract).

Tschoep et al., A Novel Glucagon/GLP-1 Co-Agonist Eliminates Obesity in Rodents, Diabetes, 58 (Supp. 1): A83 (2009).

Unson et al., "Glucagon antagonists: Contribution to binding and activity of the amino-terminal sequence 1-5, position 12 and the putative alpha-helical segment 19-27," J. Biol. Chem. v264, pp. 789-794, Jan. 15, 1989, p. 792, para 1, Table 1.

Unson et al., Positively Charged Residues at Positions 12, 17, and 18 of Glucagon Ensure Maximum Biological Potency, *J. Biol. Chem.*, 273(17): 10308-12 (1998).

Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.

Wynne et al., "Subcutaneous Oxyntomodulin Reduces Body Weight in Overweight and Obese Subjects," *Diabetes*, vol. 54, Aug. 2005, pp. 2390-2395.

Yang et al., Synthesis and Biological Assessment of Sulfonic Acid-Based Glucagon Antagonists, Understanding Biology Using Peptides, American Peptide Symposia, 9(Part 6): 305-6 (2006).

Zhang et al., Design and synthesis of novel GLP1 analogues with significantly prolonged time action, Biopolymers., 80(4): 555 (2005).

Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

Azizeh et al., "Pure glucagon antagonists: biological activities and cAMP accumulation using phosphodiesterase inhibitors," Peptides 1997, vol. 18, No. 5, pp. 633-641.

Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.

Phillips et al., "Supramolecular Protein Engineering: Design of Zinc-Stapled Insulin Hexamers As a Long Acting Depot," J. Biol. Chem., vol. 285, No. 16, Apr. 16, 2010, pp. 11755-11759.

Murphy, et al., "Potent Long-Acting Alkylated Analogs of Growth Hormone-Releasing Factor," Pept. Res., vol. 1. No. 1, pp. 36-41 (1988).

De, et al., "Investigation of the feasibily of an amide-based prodrug under physiological conditions," Int. J. Pept. Res. Ther., 14, pp. 255-262 (2008).

PCT International Search Report for PCT/US2011/041601 completed by the US Searching Authority on Nov. 10, 2011.

Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.

Gysin et al., "Design and Synthesis of Glucagon Partial Agonists and Antagonists," Biochemistry, 25, (1986), pp. 8278-8284.

PCT International Search Report for PCT/US2009/047437 completed by the US Searching Authority on Nov. 3, 2009.

Supplemental European Search Report issued in connection with EP Application No. 09767567.2 issued on Jun. 17, 2011.

Extended EP Search Report completed by the EP Searching Authority on Apr. 6, 2011 in connection with EP Patent Application No. 08845852.6.

DatabaseEMBL, Jul. 16, 2007, Richard DiMarchi and David Smiley, "Human Glucagon Peptide SEQ ID No. 1," XP002631582, retrieved from EBI, Database Accession No. AGB07042, Abstract.

Day, J.; Patterson, J.; Gelfanov, V. and DiMarchi, Richard Molecular-basis for Specificity in Biological Action at the Homologous Glucagon and GLP-1 Receptors, (2009) Proceedings of the 21$^{st}$ American Peptide Society 142-143.

De, A. and DiMarchi, R. Synthesis & Analysis of Peptide Hormone-based prodrugs, (2009) Proceedings of the 21st American Peptide Society 160-161.

De, Arnab; DiMarchi, Richard D. Investigation of the feasibility of an amide-based prodrug under physiological conditions. International Journal of Peptide Research and Therapeutics (2008), 14(4), 393.

(56) References Cited

OTHER PUBLICATIONS

De, A. and DiMarchi, R. Synthesis & Characterization of Ester-Based Prodrugs of Glucagon-Like Peptide 1, Peptide Science (2010) 94(4) 448-456.
DiMarchi, Richard, "The Use of Bioproducts in the Treatments of Metabolic Diseases" presentation slides for the Keystone Symposia (Jan. 25, 2009, Banff, Alberta).
Finan, B.; Gelfanov, V. and DiMarchi, R. Assessment of a Tat-Derived Peptide as a Vector for Hormonal Transport, (2009) Proceedings of the 21st American Peptide Society 321-322.
Kukuch, A.; Patterson, J.; DiMarchi, R. and Tolbert, T. Immunoglobulin Fc-based Peptide Fusion Proteins as a Basis for Optimizing In Vivo Pharmacology, (2009) Proceedings of the $21^{st}$ American Peptide Society 177-178.
Ma, T.; Day, J.; Gelfanov, V. and DiMarchi, R. Discovery and Structural Optimization of High Affinity Co-Agonists at the Glucagon and GLP-1 Receptors, (2009) Proceedings of the $21^{st}$ American Peptide Society 146-147.
Ouyang et al., "Synthesis and Characterization of Peptides with Glucagon Antagonism and GLP-1 Agonism," poster presentation at the $21^{st}$ American Peptide Symposium (Jun. 7-12, 2009, Bloomington, IN).
Tschoep et al., "A Novel Glucagon/GLP-1 Co-Agonist Eliminates Obesity in Rodents," American Diabetes Association Abstract No. 313-OR (2009).
Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).
Tschoep, Matthias, "Afferent Gut Hormones in the Control of Energy Balance and Metabolism" presentation slides for the 21st American Peptide Symposium (Jun. 7-12, 2009, Bloomington, IN).
Ward, B.; Finan, B.; Gelfanov, V. and DiMarchi, R. Exploring the N-terminal Hydrophobic Faces of Glucagon and Glucagon-like Peptide-1, (2009) Proceedings of the $21^{st}$ American Peptide Society 153-154.
Yang, B. and DiMarchi, R.D. (2005). A Novel Approach to Resin-based Cysteine Alkylation Peptides: Chemistry, Structure and Biology, Proceedings of the XIX American Peptide Symposium, (88-89).
Irwin et al., "Early administration of the glucose-dependent insulinotropic polypeptide receptor antagonist ($Pro^3$) GIP prevents the development of diabetes and related metabolic abnormalities associated with genetically inherited obesity in ob/ob mice," Diabetologia 50:1532-1540 (2007).
Kulkarni, "GIP: No Longer the Neglected Incretin Twin?," Science Translational Medicine 2(49): p. 47, Sep. 15, 2010.
Montrose-Rafizadeh et al., "High Potency Antagonists of the Pancreatic Glucagon-like Peptide-1 Receptor," Journal of Biological Chemistry, 272(34) 21201-21206 (1997).
Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.
Habi, "Special Issue: Program and Abstracts for the 19th American Peptide Symposium, 2005, Abstracts of Poster Section C," (pp. 574-603) Article first published online: Jun. 10, 2005 | DOI: 10.1002/bip.20325.
Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.
Vijayalakshmi et al., "Comparison of Helix-Stabilizing Effects of α, α-dialkyl Glycines with Linear and Cycloalkyl Side Chains", Biopolymers 53: 84-98 (Jan. 21, 2000).
Andrews et al., "Forming Stable Helical Peptides Using Natural and Artificial Amino Acids", Tetrahedron 55: 11711-11743, (1999).
Battersby et al., "Diketopiperazine Formation and N-Terminal Degradation in Recombinant Human Growth Hormone", International Journal of Peptide & Protein Research 44: 215-222, (1994) (Abstract).

Eriksson et al., "hPEPT1 Affinity and Translocation of Selected Gln-Sar and Glu-Sar Dipeptide Derivatives", Molecular Pharmaceutics vol. 2, No. 3: 242-249 (May 10, 2005).
Garcia-Aparicio et al., "Design and Discovery of a Novel Dipeptidyl-peptidase IV (CD26)-Based Prodrug Approach", J. Med. Chem. 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", AAPS Pharmsci 2000 2(1) article 5: 1-6 (Mar. 17, 2000).
Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).
Schafmeister et al., "An All-Hydrocarbon Cross-Linking System for Enhancing the Helicity and Metaboli Stability of Peptides", J. Am. Chem. Soc. 122: 5891-5892 (2000).
Walensky et al., "Activation of Apoptosis in Vivo by a Hydrocarbon-Stapled BH3 Helix", Science 205: 1466-1470 (Sep. 3, 2004).
Lebl, Michal, "Peptides: Breaking Away: The Proceedings of the Twenty-First American Peptide Symposium", Prompt Scientific Publishing (2009).
"Legacy Products—'Back to the Future'," presentation to Eli Lilly and Co., Sep. 22, 2005.
"Application of Chemical Biotechnology to Optimization of Endocrine Hormones," Carothers Lecture, Mar. 22, 2007.
"The Emergence of Chemical Biotechnology & Its Application to Optimization of Endocrine Hormones," UMBC presentation, Mar. 26, 2008.
"Emergence of Chemical Biotechnology," Eli Lilly and Co. presentation, Jun. 22, 2009.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," AAPS May 2010.
"Two for the Money" Gut Hormone Hybrids, Tschoep, ADA meeting, Jun. 25-29, 2010, Orlando, FL.
"Biotechnology—Basis for Better Health & Economic Prosperity," Ohio State University presentation, Aug. 28, 2010.
"Novel Glucagon-Based Peptides—Virtues of Combinatorial Pharmacology," European Peptide Symposium, Sep. 5-9, 2010, Copenhagen, Denmark.
"Biotechnology—A Basis for Better Health & Economic Prosperity," Indiana University television presentation, Nov. 2010.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Speaking From the Gut: From Gastrointestinal Hormones to Combinatorial Therapies," Presentation to American Diabetes Association, Jun. 25, 2011.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
"The Pursuit of Transformational Medicines," Keystone presentation, Jan. 29-Feb. 3, 2012, Santa Fe, NM.
"Novel Glucagon Peptides That Demonstrate the Virtues of Combinatorial Pharmacology," University of Toledo, Mar. 22, 2012.
Althage et al.,JBC "Targeted Ablation of GIP-Producing Cells in Transgenic mice reduces obesity and insulin resistance induced by a high fat diet" 2008).
Chia et al., "Exogenous glucose-dependent insulinotropic polypeptide worsens post-prandial hyperglycemia in type 2 diabetes," Diabetes, 58: 1342-1349 (2009).
Drucker, "Glucagon Gene Expression in Vertebrate Brain," The Journal of Biological Chemistry, vol. 263, No. 27, pp. 13475-13478, 1988.
Drucker, "The biology of incretin hormones," Cell Metabolism 3:153-165 (2006).
PCT International Search Report for PCT/US2009/034448 completed by the US Searching Authority on Jun. 4, 2010.

(56) References Cited

OTHER PUBLICATIONS

PCT International Search Report for PCT/US2009/068678 completed by the US Searching Authority on May 5, 2010.
Pan et al., "Synthesis of Cetuximab-Immunoliposomes via a Cholesterol-Based Membrane Anchor for Targeting of EGFR," Bioconjugate Chem., 18, pp. 101-108, 2007.
PCT International Search Report for PCT/US2009/047447 completed by the US Searching Authority on Mar. 19, 2010.
Collie et al., "Purification and sequence of rat oxyntomodulin," Proc. Natl. Acad. Sci. USA, vol. 91, pp. 9362-9366, Sep. 1994.
Sueiras-Diaz et al., "Structure-Activity Studies on the N-Terminal Region of Glucagon," J. Med. Chem., 27, pp. 310-315, 1984.
Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.
Unson et al., "Role of Histidine-1 in Glucagon Action," Archives of Biochemistry and Biophysics, vol. 300, No. 2, pp. 747-750, Feb. 1, 1993.
Sato, H., "Enzymatic procedure for site-specific pegylation of proteins," Advanced Drug Delivery Reviews 54, pp. 487-504 (2002).
"Novel Glucagon-Like Chimera Peptides—Virtues of Combinatorial Pharmacology," University of Cincinnati, Jun. 2010.
"Molecular Miracles," Indiana University, Apr. 13, 2011.
"Novel Glucagon-Based Peptides—Virtues of Combinatorial Pharmacology," Aug. 31, 2011, Berlin.
Ward, "Fatty Acid Acylation of Peptides: Developing strategies to enhance medicines for treating metabolic disorders," Jan. 14, 2009.
DiMarchi, "Peptides—Development of Prodrug Chemistry," RBF Symposium Feb. 1-4, 2011 India.
Tschoep, "CNS Integration of Systems Metabolism: Target Opportunities for Diabetes Prevention and Therapy," RBF Symposium Feb. 1-4, 2011 India.
Yang et al., "Synthesis and Biological Assessment of Sulfonic Acid-Based Glucagon Antagonists," poster presentation to American Peptide Society, 2005.
Yang et al., "A Novel Approach to Resin-Based Cysteine Alkylation," poster presentation to American Peptide Society, 2005.
PCT International Search Report for PCT/US2010/038825 completed by the US Searching Authority on Sep. 15, 2010.
PCT International Search Report for PCT/US2010/059724 completed by the US Searching Authority on Jun. 14, 2011.
Wibowo, Synthesis, Purification , and Biological Activity of AIB Substituted Glucagon and GLP-1 Peptide Analogues (2005-2006) vol. 45, 707=738, accessed https://scholarworks.iu.edu/dspce/handle/2022/326 on Jul. 17, 2012.
O'Brien, Assay for DPPIV Activity using Homogenous, Luminescent Method, Cell Notes 2005, 11:8-11.
Evans et al., "Effect of β-Endorphin C-Terminal Peptides on Glucose Uptake in Isolated Skeletal Muscles of the Mouse," Peptides, vol. 18, No. 1, pp. 165-167, (1997).
Hansen et al., "Incretin hormones and insulin sensitivity," Trends in Endocrinology and Metabolism, vol. 16, No. 4, May/Jun. 2005, pp. 135-136.
Jen Holst "The Physiology of Glucagon -like Peptide -1", Physiological Reviews, V. 87, No. 4, pp. 1409-1439 (Oct. 2007).
Database Geneseq [Online] Feb. 16, 2012, Human glucagonanalog peptide SEQ:495, XP002710329, EBI accession No. GSP: AZQ99373, Database accession No. AZQ99373.
Azizeh et al., "The role of phenylalanine at position 6 in glucagon's mechanism of biological action: multiple replacement analogues of glucagon" J Med Chem 1997, 40, 2555-2562.
Supplemental EP Search report for EP09800752 completed on Jul. 20, 2011.
"Novel Glucagon-Like Chimera Peptides—Virtues of Combinatorial Pharmacology," AAPS 2005 San Francisco.
Zhou et al., "Peptide and protein drugs: I. Therapeutic applications, absorption and parenteral administration," International Journal of Pharmaceutics vol. 75 p. 97-111 (Sep. 20, 1991).
PCT International Search Report and Written Opinion completed by the ISA/KR on Jan. 30, 2013 and issued in connection with PCT/US2012/042085.
Day, Jonathan W. et al., 'Charge inversion at position 68 of the glucagon and glucagon-like peptide-1 receptors supports selectivity in hormone action', Journal of Peptide Science, Nov. 30, 2010, vol. 17, No. 3, pp. 218-225, ISSN 1099-1387. See Abstract: Figs. 1-2.
Day, Jonathan W. et al., 'A new glucagon and GLP-I co-agonist eliminates obesity in rodents', Nature Chemical Biology, Oct. 2009, vol. 5, No. 10, pp. 749-757, ISSN 1552-4450. See p. 2, left column, paragraph 2: Fig. 1.
Patterson, James T. et al., 'Functional association of the N-terminal residues with the central region in glucagon-related peptides', Journal of Peptide Science, First published online Jun. 10, 2011, vol. 17, No. 10, pp. 659-666, ISSN 1099-1387. See Abstract: Fig. 1.

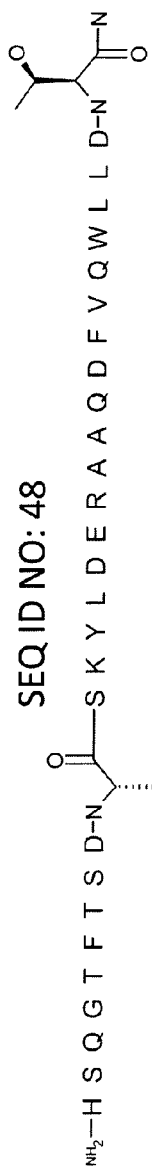

SEQUENCE LISTING

```
<160> NUMBER OF SEQ ID NOS: 65

<210> SEQ ID NO 1
<211> LENGTH: 29
<212> TYPE: PRT
<213> ORGANISM: Homo sapiens
<220> FEATURE:
<221> NAME/KEY: MISC_FEATURE
<223> OTHER INFORMATION: Native human glucagon

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
```

```
            20                  25

<210> SEQ ID NO 2
<211> LENGTH: 37
<212> TYPE: PRT
<213> ORGANISM: Homo sapiens
<220> FEATURE:
<221> NAME/KEY: MISC_FEATURE
<223> OTHER INFORMATION: GLP-1

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 3
<211> LENGTH: 33
<212> TYPE: PRT
<213> ORGANISM: Homo sapiens
<220> FEATURE:
<221> NAME/KEY: MISC_FEATURE
<223> OTHER INFORMATION: GLP-2

<400> SEQUENCE: 3

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 4
<211> LENGTH: 37
<212> TYPE: PRT
<213> ORGANISM: Homo sapiens
<220> FEATURE:
<221> NAME/KEY: MISC_FEATURE
<223> OTHER INFORMATION: Oxyntomodulin

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Arg Asn Asn Ile Ala
        35

<210> SEQ ID NO 5
<211> LENGTH: 30
<212> TYPE: PRT
<213> ORGANISM: Homo sapiens
<220> FEATURE:
<221> NAME/KEY: MISC_FEATURE
<223> OTHER INFORMATION: GLP1 (7-36 amide)
<220> FEATURE:
<221> NAME/KEY: MOD_RES
<222> LOCATION: (30)..(30)
<223> OTHER INFORMATION: C-terminal amidation

<400> SEQUENCE: 5

His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg
            20                  25                  30

<210> SEQ ID NO 6
<211> LENGTH: 31
<212> TYPE: PRT
<213> ORGANISM: Homo sapiens
<220> FEATURE:
<221> NAME/KEY: MISC_FEATURE
<223> OTHER INFORMATION: GLP-1 (7-37 acid)

<400> SEQUENCE: 6

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 7
<211> LENGTH: 39
<212> TYPE: PRT
<213> ORGANISM: Heloderma suspectum
<220> FEATURE:
<221> NAME/KEY: MISC_FEATURE
<223> OTHER INFORMATION: Exendin-4

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Lys Arg Asn Arg Asn Asn Ile Ala
 1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Gly Pro Ser Ser Gly Ala Pro Pro Pro Ser
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Gly Gly Pro Ser Ser Gly Ala Pro Pro Pro Ser
 1               5                  10
```

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Lys Arg Asn Arg
1

<210> SEQ ID NO 12

<400> SEQUENCE: 12

000

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 13

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Asp Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 14

His Xaa Gln Gly Thr Phe Thr Ser Asp Tyr Ser Lys Tyr Leu Asp Glu
1               5                   10                  15

Arg Arg Ala Xaa Glu Phe Val Cys Trp Leu Leu Asp Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 15

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Met Asp Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 16

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Asp Glu
            20                  25

<210> SEQ ID NO 17

```
<400> SEQUENCE: 17

000

<210> SEQ ID NO 18

<400> SEQUENCE: 18

000

<210> SEQ ID NO 19
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (31)..(31)
<223> OTHER INFORMATION: C-terminal amidation

<400> SEQUENCE: 19

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Arg Gly
            20                  25                  30

<210> SEQ ID NO 20
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: desamino-His
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 20

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 21
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl-His
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 21

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 22
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 22

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Gly Arg Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
```

```
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 23

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Lys Gly Arg Gly
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 24

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Lys Asp Gly Arg Gly
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 25

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Lys Asp Gly Arg Pro
```

<210> SEQ ID NO 26
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (28)..(28)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 26

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Lys Xaa Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (31)..(31)
<223> OTHER INFORMATION: C-terminal amidation

<400> SEQUENCE: 27

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Lys Gly Arg Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser

```
<220> FEATURE:
<221> NAME/KEY: MISC_FEATURE
<222> LOCATION: (10)..(10)
<223> OTHER INFORMATION: Acylated with a C16 fatty acyl group vis gamma-
      Glu spacer
<220> FEATURE:
<221> NAME/KEY: MISC_FEATURE
<222> LOCATION: (31)..(31)
<223> OTHER INFORMATION: C-terminal amidation

<400> SEQUENCE: 28

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Arg Lys
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (28)..(28)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 29

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Xaa Gly Arg Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation
```

<400> SEQUENCE: 30

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Gly Arg Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB

<400> SEQUENCE: 31

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Lys Gly Arg Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (31)..(31)
<223> OTHER INFORMATION: D-Ala
<220> FEATURE:
<221> NAME/KEY: MISC_FEATURE
<222> LOCATION: (31)..(31)
<223> OTHER INFORMATION: d-Ala

<400> SEQUENCE: 32

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Ala
            20                  25                  30

<210> SEQ ID NO 33
<211> LENGTH: 31
<212> TYPE: PRT

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (28)..(28)
<223> OTHER INFORMATION: Xaa is Orn
<220> FEATURE:
<221> NAME/KEY: MOD_RES
<222> LOCATION: (30)..(30)
<223> OTHER INFORMATION: Xaa is Orn

<400> SEQUENCE: 33

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Xaa Thr Xaa Glu
            20                  25                  30

<210> SEQ ID NO 34

<400> SEQUENCE: 34

000

<210> SEQ ID NO 35
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (39)..(39)
<223> OTHER INFORMATION: C-terminal amidation

<400> SEQUENCE: 35

His Xaa Gln Gly Thr Phe Thr Ser Asp Tyr Ser Lys Tyr Leu Asp Glu
1               5                   10                  15

Arg Arg Ala Xaa Glu Phe Val Cys Trp Leu Leu Asp Gly Gly Pro Ser
            20                  25                  30

Ser Gly Ala Pro Pro Pro Ser
        35

<210> SEQ ID NO 36
```

```
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 36

His Xaa Gln Gly Thr Phe Thr Ser Asp Lys Ser Lys Tyr Leu Asp Xaa
1               5                   10                  15
Arg Ala Ala Gln Asp Phe Val Gln Trp Leu Lys Asp Gly Arg Gly
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (31)..(31)
<223> OTHER INFORMATION: D-Glu

<400> SEQUENCE: 37

His Xaa Gln Gly Thr Phe Thr Ser Asp Lys Ser Lys Tyr Leu Asp Xaa
1               5                   10                  15
Arg Ala Ala Gln Asp Phe Val Gln Trp Leu Met Lys Thr Lys Glu
            20                  25                  30

<210> SEQ ID NO 38
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
```

```
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 38

His Xaa Gln Gly Thr Phe Thr Ser Asp Tyr Ser Lys Tyr Leu Asp Xaa
1               5                   10                  15

Lys Arg Ala Xaa Glu Phe Val Cys Trp Leu Leu Asp Thr
            20                  25

<210> SEQ ID NO 39
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (28)..(28)
<223> OTHER INFORMATION: Covalently bound to 40kDa PEG via thioether
      made by reaction of free thiol peptide with a iodoacetic-
      functioned PEG

<400> SEQUENCE: 39

His Xaa Gln Gly Thr Phe Thr Ser Asp Tyr Ser Lys Tyr Leu Asp Xaa
1               5                   10                  15

Lys Arg Ala Lys Glu Phe Val Gln Trp Leu Leu Cys Thr
            20                  25

<210> SEQ ID NO 40
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (30)..(30)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (30)..(30)
<223> OTHER INFORMATION: C-terminal amidation
```

<400> SEQUENCE: 40

His Xaa Gln Gly Thr Phe Thr Ser Asp Tyr Ser Lys Tyr Leu Asp Xaa
1               5                   10                  15

Lys Arg Ala Lys Glu Phe Val Gln Trp Leu Leu Asp Thr Cys
            20                  25                  30

<210> SEQ ID NO 41
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MOD_RES
<222> LOCATION: (28)..(28)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 41

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Xaa Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MOD_RES
<222> LOCATION: (24)..(24)
<223> OTHER INFORMATION: Xaa is AIB
<220> FEATURE:
<221> NAME/KEY: MISC_FEATURE
<222> LOCATION: (28)..(28)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 42

His Xaa Gln Gly Thr Phe Thr Ser Asp Tyr Ser Lys Tyr Leu Asp Glu

```
1               5                   10                  15

Lys Arg Ala Xaa Glu Phe Val Xaa Trp Leu Leu Cys Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (24)..(24)
<223> OTHER INFORMATION: Covalently bound to 12kDa PEG via maleimido-
      thioether made by reaction of free thiol peptide with a maleimido-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 43

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (24)..(24)
<223> OTHER INFORMATION: Covalently bound to 20kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 44

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 45
<211> LENGTH: 29
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG

<400> SEQUENCE: 45

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Asp Thr
            20                  25

<210> SEQ ID NO 46
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (39)..(39)
<223> OTHER INFORMATION: C-terminal amidation

<400> SEQUENCE: 46

His Xaa Gln Gly Thr Phe Thr Ser Asp Tyr Ser Lys Tyr Leu Asp Xaa
1               5                   10                  15

Lys Arg Ala Xaa Glu Phe Val Cys Trp Leu Leu Asp Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
```

```
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (39)..(39)
<223> OTHER INFORMATION: C-terminal amidation

<400> SEQUENCE: 47

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Asp Gly Gly Pro Ser
            20                  25                  30

Ser Gly Ala Pro Pro Pro Ser
        35

<210> SEQ ID NO 48
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with adamantylacetyl via gamma-Glu
      spacer
<220> FEATURE:
<221> NAME/KEY: MISC_FEATURE
<222> LOCATION: (29)..(29)
<223> OTHER INFORMATION: C-terminal amidation

<400> SEQUENCE: 48

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 49
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Acylated with benzoylpropionyl
<220> FEATURE:
<221> NAME/KEY: MISC_FEATURE
<222> LOCATION: (39)..(39)
<223> OTHER INFORMATION: C-terminal amidation

<400> SEQUENCE: 49

His Ser Gln Gly Thr Phe Thr Ser Asp Lys Ser Lys Tyr Leu Asp Glu
1               5                   10                  15
```

```
Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 50
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (24)..(24)
<223> OTHER INFORMATION: Covalently bound to CH2CONH2 group
<220> FEATURE:
<221> NAME/KEY: MISC_FEATURE
<222> LOCATION: (24)..(29)
<223> OTHER INFORMATION: Side chains bound via lactam ring
<220> FEATURE:
<221> NAME/KEY: MISC_FEATURE
<222> LOCATION: (29)..(29)
<223> OTHER INFORMATION: C-terminal amidation

<400> SEQUENCE: 50

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 51
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MOD_RES
<222> LOCATION: (28)..(28)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 51

His Xaa Gln Gly Thr Phe Thr Ser Asp Tyr Ser Lys Tyr Leu Asp Glu
1               5                   10                  15

Lys Arg Ala Xaa Glu Phe Val Cys Trp Leu Leu Xaa Gly Gly Pro Ser
            20                  25                  30

Ser Gly Ala Pro Pro Ser
        35
```

<210> SEQ ID NO 52
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (18)..(18)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 52

His Xaa Gln Gly Thr Phe Thr Ser Asp Tyr Ser Lys Tyr Leu Asp Glu
1               5                   10                  15

Lys Xaa Ala Lys Glu Phe Val Cys Trp Leu Leu Asp Thr
            20                  25

<210> SEQ ID NO 53

<400> SEQUENCE: 53

000

<210> SEQ ID NO 54
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of free thiol peptide with a iodoacetic-
      functioned PEG
<220> FEATURE:
<221> NAME/KEY: MISC_FEATURE
<222> LOCATION: (29)..(29)
<223> OTHER INFORMATION: C-terminal amidation

<400> SEQUENCE: 54

His Xaa Gln Gly Thr Phe Thr Ser Asp Tyr Ser Lys Tyr Leu Asp Glu
1               5                   10                  15

Lys Arg Ala Xaa Asp Phe Val Cys Trp Leu Leu Asp Thr
            20                  25

<210> SEQ ID NO 55
<211> LENGTH: 39
<212> TYPE: PRT

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (10)..(10)
<223> OTHER INFORMATION: Covalently bound to Ethylene-diamine-
      tetraacetic acid amide
<220> FEATURE:
<221> NAME/KEY: MISC_FEATURE
<222> LOCATION: (39)..(39)
<223> OTHER INFORMATION: C-terminal amidation

<400> SEQUENCE: 55

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 56
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 56

His Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 57

<400> SEQUENCE: 57

000

<210> SEQ ID NO 58
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group
```

```
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 58

His Xaa Gln Gly Thr Phe Thr Ser Asp Lys Ser Lys Tyr Leu Asp Ser
1               5                   10                  15

Arg Arg Ala Xaa Asp Phe Val Gln Trp Leu Met Asn Thr
            20                  25

<210> SEQ ID NO 59
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group
<220> FEATURE:
<221> NAME/KEY: MOD_RES
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 59

His Xaa Gln Gly Thr Phe Thr Ser Asp Lys Ser Lys Tyr Leu Asp Glu
1               5                   10                  15

Arg Arg Ala Xaa Asp Phe Val Gln Trp Leu Met Asn Thr
            20                  25

<210> SEQ ID NO 60
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (31)..(31)
<223> OTHER INFORMATION: D-Glu

<400> SEQUENCE: 60

His Xaa Gln Gly Thr Phe Thr Ser Asp Lys Ser Lys Tyr Leu Asp Xaa
1               5                   10                  15
```

Arg Ala Ala Gln Asp Phe Val Gln Trp Leu Met Lys Thr Lys Glu
            20                  25                  30

<210> SEQ ID NO 61
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 61

His Xaa Gln Gly Thr Phe Thr Ser Asp Lys Ser Lys Tyr Leu Asp Glu
1               5                   10                  15
Arg Ala Ala Gln Asp Phe Val Gln Trp Leu Met Asp Thr
            20                  25

<210> SEQ ID NO 62
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      N-methyl Ala, or AIB
<220> FEATURE:
<221> NAME/KEY: MISC_FEATURE
<222> LOCATION: (39)..(39)
<223> OTHER INFORMATION: C-terminal amidation

<400> SEQUENCE: 62

His Xaa Gln Gly Thr Phe Thr Ser Asp Tyr Ser Lys Tyr Leu Asp Glu
1               5                   10                  15
Gln Ala Val Arg Leu Phe Ile Cys Trp Leu Leu Asp Gly Gly Pro Ser
            20                  25                  30
Ser Gly Ala Pro Pro Pro Ser
        35

<210> SEQ ID NO 63
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains at position 16
      and 20
<220> FEATURE:
<221> NAME/KEY: MISC_FEATURE
<222> LOCATION: (24)..(24)

```
<223> OTHER INFORMATION: Covalently bound to CH2CONH2 group
<220> FEATURE:
<221> NAME/KEY: MISC_FEATURE
<222> LOCATION: (29)..(29)
<223> OTHER INFORMATION: C-terminal amidation

<400> SEQUENCE: 63

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 64
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      N-methyl Ala, or AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 64

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 65
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      N-methyl Ala, or AIB
<220> FEATURE:
<221> NAME/KEY: MISC_FEATURE
<222> LOCATION: (10)..(10)
<223> OTHER INFORMATION: Acylated with a C16 fatty acyl group via gamma-
      Glu spacer
<220> FEATURE:
<221> NAME/KEY: MISC_FEATURE
<222> LOCATION: (30)..(30)
<223> OTHER INFORMATION: C-terminal amidation

<400> SEQUENCE: 65

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30
```

GLUCAGON/GLP-1 RECEPTOR CO-AGONISTS

CROSS REFERENCE TO RELATED APPLICATIONS

This application is a U.S. national counterpart application of international application serial No. PCT/US2012/042085 filed Jun. 12, 2012, which claims priority to U.S. Provisional Patent Application No. 61/500,025 filed Jun. 22, 2011. The entire disclosures of PCT/US2012/042085 and USSN 61/500,025 are hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 38 kilobytes ACII (Text) file named "07012J_PCT_SeqListing.txt," created on Jun. 11, 2012.

BACKGROUND

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1(7-36) amide or GLP-1(7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

SUMMARY

The present disclosures provide peptides and variant peptides that exhibit activity at the glucagon receptor, activity at the GLP-1 receptor, or activity at each of the glucagon receptor and the GLP-1 receptor. In exemplary embodiments, the presently disclosed peptides and variant peptides exhibit enhanced activity at the GLP-1 receptor, as compared to native glucagon. In exemplary aspects, the peptides and variant peptides exhibit at least 100-fold selectivity for the human GLP-1 receptor versus the GIP receptor.

The present disclosures further provide conjugates comprising any of the peptides and variant peptides described herein conjugated to a heterologous moiety. In exemplary aspects, the heterologous moiety is a peptide or protein and the conjugate is a fusion peptide or chimeric peptide. In exemplary aspects, the heterologous moiety is a polymer, e.g., a polyethylene glycol. The present disclosures furthermore provide dimers and multimers comprising any of the peptides and variant peptides described herein.

The present disclosures moreover provides pharmaceutical compositions comprising any of the peptides and variant peptides described herein and a pharmaceutically acceptable carrier, as well as a method of treating or preventing a disease or medical condition (e.g., metabolic syndrome, diabetes, obesity, liver steatosis, a neurodegenerative disease, hypoglycemia) in a patient. The method comprises administering to the patient a presently disclosed peptide or peptide variant, optionally formulated into a pharmaceutical composition, in an amount effective to treat the disease or medical condition.

BRIEF DESCRIPTION OF THE DRAWINGS

FIG. 1 represents the structure of two glucagon analogs. The first glucagon analog has a D-serine at position 2 and is acylated with adamantylacetyl via gamma-Glu spacer at position 10 (SEQ ID NO: 48). The second glucagon analog has a D-serine at position 2 and is acylated with benzoylpropionyl at position 10 (SEQ ID NO: 49).

DETAILED DESCRIPTION

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

As used herein, the term "peptide" encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length.

Typically, polypeptides and proteins have a polymer length that is greater than that of "peptides."

Throughout the application, all references to a particular amino acid position by number (e.g., position 28) refer to the amino acid at that position in native glucagon (SEQ ID NO: 1) or the corresponding amino acid position in any analogs thereof. For example, a reference herein to "position 28" would mean the corresponding position 27 for a glucagon analog in which the first amino acid of SEQ ID NO: 1 has been deleted. Similarly, a reference herein to "position 28" would mean the corresponding position 29 for a glucagon analog in which one amino acid has been added before the N-terminus of SEQ ID NO: 1. As used herein an "amino acid modification" refers to (i) a substitution or replacement of an amino acid of SEQ ID NO: 1 with a different amino acid (naturally-occurring or coded or non-coded or non-naturally-occurring amino acid), (ii) an addition of an amino acid (naturally-occurring or coded or non-coded or non-naturally-occurring amino acid), to SEQ ID NO: 1 or (iii) a deletion of one or more amino acids of SEQ ID NO: 1.

"Percent identity" with respect to two amino acid sequences refers to the number of amino acids of the first sequence that match (are identical to) the amino acids in the second reference sequence, divided by the length of the reference sequence, when the two sequences are aligned to achieve maximum correspondence (e.g. gaps can be introduced for optimal alignment).

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:
   Ala, Ser, Thr, Pro, Gly;
II. Polar, negative-charged residues and their amides and esters:
   Asp, Asn, Glu, Gln, cysteic acid and homocysteic acid;
III. Polar, positive-charged residues:
   His, Arg, Lys; Ornithine (Orn)
IV. Large, aliphatic, nonpolar residues:
   Met, Leu, Ile, Val, Cys, Norleucine (Nle), homocysteine
V. Large, aromatic residues:
   Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including, for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: EC50 of the molecule at the second receptor divided by the EC50 of the molecule at the first receptor. For example, a molecule that has an EC50 of 1 nM at a first receptor and an EC50 of 100 nM at a second receptor has 100-fold selectivity for the first receptor relative to the second receptor.

As used herein the term "native glucagon" refers to a peptide consisting of the sequence of SEQ ID NO: 1 and the term "native GLP-1" is a generic term that designates GLP-1(7-36) amide, GLP-1(7-37) acid or a mixture of those two compounds.

As used herein, "glucagon potency" or "potency compared to native glucagon" of a molecule refers to the inverse ratio of the EC50 of the molecule at the glucagon receptor divided by the EC50 of native glucagon at glucagon receptor.

As used herein, "GLP-1 potency" or "potency compared to native GLP-1" of a molecule refers to the inverse ratio of the EC50 of the molecule at GLP-1 receptor divided by the EC50 of native GLP-1 at GLP-1 receptor.

Embodiments

The present disclosures provide peptides and variant peptides that exhibit activity at the GLP-1 receptor, at the glucagon receptor, or at both the GLP-1 receptor and the glucagon receptor. In this regard, the present disclosures provide GLP-1 receptor agonist peptides, glucagon receptor agonist peptides, and GLP-1/glucagon receptor co-agonist peptides. In exemplary embodiments, the presently disclosed peptides and variant peptides exhibit enhanced activity or greater potency at the GLP-1 receptor, as compared to native human glucagon (SEQ ID NO: 1). In exemplary embodiments, the peptides and variant peptides of the present disclosures exhibit greater potency at the GLP-1 receptor as compared to native human GLP-1 (SEQ ID NO: 2) or one of the active forms thereof (SEQ ID NOs: 5 and 6). In exemplary embodiments, the peptides and variant peptides exhibit greater potency at the glucagon receptor compared to native human GLP-1. In exemplary embodiments, the peptides and variant peptides exhibit greater potency at the glucagon receptor compared to native human glucagon.

In exemplary embodiments, the peptides and variant peptides described herein exhibit other improvements in properties relative to native glucagon or native GLP-1, such as greater stability, greater solubility, a prolonged half-life in circulation, a delayed onset of action, an extended duration of action, a dampened peak (e.g., relatively decreased mean peak plasma concentration), and an improved resistance to proteases, such as DPP-IV.

The peptides and variant peptides described herein are based on the amino acid sequence of native human glucagon (SEQ ID NO: 1), and are described herein as "peptides", "variant peptides", "glucagon analogs", "analogs", or "glucagon peptides." It is understood that terms such as "analog" or "variant" or "modifications" encompass peptides or proteins synthesized de novo and do not require the performance of any particular modification step. In some aspects, the peptides and variant peptides described herein comprise a modified amino acid sequence of SEQ ID NO: 1 comprising 1, 2, 3, 4, 5, 6, 7, 8, 9, 10, 11, 12, 13, 14, 15 amino acid modifications relative to SEQ ID NO: 1, and in some instances, 16 or more (e.g., 17, 18, 19, 20, 21, 22, 23, 24, 25, 26), amino acid modifications, as further described herein. The following description of glucagon analogs and/or glucagon peptides thus applies to any of the presently disclosed peptides and variant peptides, regardless of the degree of similarity between native human glucagon (SEQ ID NO: 1) and the peptide or variant peptide of the present disclosures.

It is contemplated that any of the peptide sequences described herein may be further varied by incorporating additional amino acid modifications; for example, by including any of the modifications described herein, e.g., at the positions described herein, or by incorporating conservative substitutions, or by returning to the native glucagon amino acid (see SEQ ID NO: 1) at that position. In exemplary embodiments, the modifications include, e.g., acylation, alkylation, pegylation, truncation at C-terminus, substitution of the amino acid at one or more of positions 1, 2, 3, 7, 10, 12, 15, 16, 17, 18, 19, 20, 21, 23, 24, 27, 28, and 29. For example, where any of the peptide sequences disclosed herein includes a Cys for purposes of pegylation, a variant peptide may use a different amino acid for pegylation. As another example, a variant peptide may be pegylated at a different position (e.g., replacing the existing Cys with a different amino acid, inserting a new Cys at the proposed pegylation position, and pegylating the new Cys). As yet a further example, where any of the peptide sequences disclosed herein includes a Lys for purposes of acylation, the Lys may be moved to a different position and the new position acylated. In any of the embodiments described herein, the variant peptides may be, for example, 80%, 85%, 90% or 95% identical to the parent peptides over the length of the parent peptides or over amino acids 1-29 of the parent peptide (e.g., may incorporate 1, 2, 3, 4, or 5 additional modifications compared to the parent peptide).

Conjugates, fusion proteins and multimers of any of the peptide sequences disclosed herein are also contemplated.

Activity of the Peptides and Variant Peptides

Agonist Activity at the Glucagon Receptor

In exemplary embodiments, the peptides and variant peptides of the present disclosures exhibit an EC50 at the glucagon receptor of about 1000 μM or less (e.g., about 750 μM or less, about 500 μM or less, about 250 μM or less, about 100 μM or less, about 75 μM or less, about 50 μM or less, about 25 μM or less, about 10 μM or less, about 5 μM or less, or about 1 μM or less). In exemplary embodiments, the peptides and variant peptides exhibit an EC50 for glucagon receptor activation which is in the nanomolar range. For example, the presently disclosed peptides and variant peptides exhibit an EC50 at the glucagon receptor which is about 1000 nM or less (e.g., about 750 nM or less, about 500 nM or less, about 250 nM or less, about 100 nM or less, about 75 nM or less, about 50 nM or less, about 25 nM or less, about 10 nM or less, about 5 nM or less, or about 1 nM or less). In exemplary embodiments, the peptides and variant peptides exhibit an EC50 at the glucagon receptor which is in the picomolar range. Accordingly, in exemplary aspects, the peptides and variant peptides exhibit an EC50 for glucagon receptor activation of about 1000 pM or less (e.g., about 750 pM or less, about 500 pM or less, about 250 pM or less, about 100 pM or less, about 75 pM or less, about 50 pM or less, about 25 pM or less, about 10 pM or less, about 5 pM or less, or about 1 pM or less). It is understood that a lower EC50 indicates higher activity or potency at the receptor.

In some embodiments, the glucagon analogs described herein exhibit an EC50 at the glucagon receptor that is about 0.001 pM or more, about 0.01 pM or more, or about 0.1 pM or more. Glucagon receptor activation (glucagon receptor activity) can be measured by in vitro assays measuring cAMP induction in HEK293 cells over-expressing the glucagon receptor, e.g., assaying HEK293 cells co-transfected with DNA encoding the glucagon receptor and a luciferase gene linked to cAMP responsive element as described in Example 2.

In exemplary embodiments, the presently disclosed peptides and variant peptides exhibit about 0.001% or more, about 0.01% or more, about 0.1% or more, about 0.5% or more, about 1% or more, about 5% or more, about 10% or more, about 20% or more, about 30% or more, about 40% or more, about 50% or more, about 60% or more, about 75% or more, about 100% or more, about 125% or more, about 150% or more, about 175% or more, about 200% or more, about 250% or more, about 300% or more, about 350% or more, about 400% or more, about 450% or more, or about 500% or higher activity at the glucagon receptor relative to native glucagon (glucagon potency). In some embodiments, the peptides and variant peptides described herein exhibit about 5000% or less or about 10,000% or less activity at the glucagon receptor relative to native glucagon. A glucagon analog's activity at a receptor relative to a native ligand of the receptor is calculated as the inverse ratio of EC50s for the glucagon analog vs. the native ligand.

In some embodiments, the peptides and variant peptides exhibit substantial activity (potency) at only the glucagon receptor and little to no activity at the GLP-1 receptor. Accordingly, in some embodiments, the peptides and variant peptides are considered as "pure glucagon receptor agonists" or are not considered as a "glucagon/GLP-1 receptor co-agonist." In some embodiments these peptides and variant peptides exhibit any of the levels of activity or potency at the glucagon receptor described herein but have substantially less activity (potency) at the GLP-1 receptor. In some embodiments, the glucagon analog exhibits an EC50 at the GLP-1 receptor which is 100-fold or greater than the EC50 at the glucagon receptor.

Agonist Activity at the GLP-1 Receptor

In exemplary embodiments, the peptides and variant peptides exhibit an EC50 for GLP-1 receptor activation of about 1000 µM or less (e.g., about 750 µM or less, about 500 µM or less, about 250 µM or less, about 100 µM or less, about 75 µM or less, about 50 µM or less, about 25 µM or less, about 10 µM or less, about 5 µM or less, or about 1 µM or less). In exemplary embodiments, the peptides and variant peptides exhibit an EC50 at the GLP-1 receptor of about 1000 nM or less (e.g., about 750 nM or less, about 500 nM or less, about 250 nM or less, about 100 nM or less, about 75 nM or less, about 50 nM or less, about 25 nM or less, about 10 nM or less, about 5 nM or less, or about 1 nM or less). In exemplary embodiments, the peptides and variant peptides has an EC50 at the GLP-1 receptor which is in the picomolar range. Accordingly, in some embodiments, the peptides and variant peptides exhibit an EC50 for GLP-1 receptor activation of about 1000 pM or less (e.g., about 750 pM or less, about 500 pM or less, about 250 pM or less, about 100 pM or less, about 75 pM or less, about 50 pM or less, about 25 pM or less, about 10 pM or less, about 5 pM or less, or about 1 pM or less). It is understood that a lower EC50 indicates higher activity or potency at the receptor.

In exemplary embodiments, the peptides and variant peptides described herein exhibit an EC50 at the GLP-1 receptor that is about 0.001 pM or more, about 0.01 pM or more, or about 0.1 pM or more. GLP-1 receptor activation (GLP-1 receptor activity) can be measured by in vitro assays measuring cAMP induction in HEK293 cells over-expressing the GLP-1 receptor, e.g., assaying HEK293 cells co-transfected with DNA encoding the GLP-1 receptor and a luciferase gene linked to cAMP responsive element as described in Example 2.

In some embodiments, the peptides and variant peptides of the present disclosures exhibit about 0.001% or more, about 0.01% or more, about 0.1% or more, about 0.5% or more, about 1% or more, about 5% or more, about 10% or more, about 20% or more, about 30% or more, about 40% or more, about 50% or more, about 60% or more, about 75% or more, about 100% or more, about 125% or more, about 150% or more, about 175% or more, about 200% or more, about 250% or more, about 300% or more, about 350% or more, about 400% or more, about 450% or more, or about 500% or higher activity at the GLP-1 receptor relative to native GLP-1 (GLP-1 potency). In some embodiments, the peptides and variant peptides described herein exhibit about 5000% or less or about 10,000% or less activity at the GLP-1 receptor relative to native GLP-1 (GLP-1 potency).

In some embodiments, the peptides and variant peptides exhibit substantial activity (potency) at only the GLP-1 receptor and little to no activity at the glucagon receptor. In some embodiments, the peptides and variant peptides are considered as "pure GLP-1 receptor agonists" or are not considered as "glucagon/GLP-1 receptor co-agonists." In some embodiments these peptides and variant peptides exhibit any of the levels of activity or potency at the GLP-1 receptor described herein but have substantially less activity (potency) at the glucagon receptor. In some embodiments, the peptides and variant peptides exhibit an EC50 at the glucagon receptor which is 100-fold or greater than the EC50 at the GLP-1 receptor.

Agonist Activity at the GLP-1 Receptor and the Glucagon Receptor

In exemplary embodiments, the peptides and variant peptides exhibit activity at both the GLP-1 receptor and glucagon receptor and may be considered as "glucagon/GLP-1 receptor co-agonists". In exemplary embodiments, the activity (e.g., the EC50 or the relative activity or potency) of the peptides and variant peptides at the glucagon receptor is within about 50-fold, about 40-fold, about 30-fold, about 20-fold, about 10-fold, or about 5 fold different (higher or lower) from its activity (e.g., the EC50 or the relative activity or potency) at the GLP-1 receptor. In exemplary aspects, the glucagon potency of the peptide or variant peptide is within about 25-, about 20-, about 15-, about 10-, or about 5-fold different (higher or lower) from its GLP-1 potency. In exemplary aspects, the glucagon potency of the peptide or variant peptide is within about 25-, about 20-, about 15-, about 10-, or about 5-fold lower from its GLP-1 potency.

In exemplary embodiments, the co-agonist is approximately equipotent or relatively more potent at the GLP-1 receptor than the glucagon receptor. For example, the ratio of the relative activity or the EC50 or the potency of the peptide or variant peptide at the glucagon receptor divided by the relative activity or the EC50 or potency of the peptide or variant peptide at the GLP-1 receptor is less than, or is about, X, wherein X is selected from 100, 75, 60, 50, 40, 30, 20, 15, 10, or 5. In exemplary embodiments, the ratio of the EC50 or potency or relative activity of the peptide or variant peptide at the glucagon receptor divided by the EC50 or potency or relative activity of the peptide or variant peptide at the GLP-1 receptor is about 1 and less than 5 (e.g., about 4, about 3, about 2, about 1). In exemplary embodiments, the ratio of the EC50 or potency or relative activity of the peptide or variant peptide at the GLP-1 receptor divided by the EC50 or potency or relative activity of the peptide or variant peptide at the glucagon receptor is less than 5 (e.g., about 4, about 3, about 2, about 1). In exemplary embodiments, the ratio of the glucagon potency of the peptide or variant peptide compared to the GLP-1 potency of the peptide or variant peptide is less than, or is about, Y, wherein Y is selected from 100, 75, 60, 50, 40, 30, 20, 15, 10, and 5. In exemplary embodiments, the ratio of the glucagon potency of the peptide or variant peptide compared to the GLP-1 potency of the peptide or variant peptide is less than 5 (e.g., about 4, about 3, about 2, about 1). In some embodiments, the glucagon analog has an EC50 at the glucagon receptor which is 2- to 10-fold (e.g., 2-fold, 3-fold, 4-fold, 5-fold, 6-fold, 7-fold, 8-fold, 9-fold, 10-fold) greater than the EC50 at the GLP-1 receptor.

In exemplary embodiments, the peptide is primarily a glucagon agonist and is relatively more potent at the glucagon receptor than the GLP-1 receptor (e.g. the peptide is 5 times or more potent at the glucagon receptor compared to the GLP-1 receptor). For example, the ratio of the relative activity or potency or the EC50 of the peptide or variant peptide at the GLP-1 receptor divided by the relative activity or potency or the EC50 of the peptide or variant peptide at the glucagon receptor is less than, or is about, V, wherein V is selected from 100, 75, 60, 50, 40, 30, 20, 15, 10, or 5. In some embodiments, the ratio of the GLP-1 potency of the peptide or variant peptide compared to the glucagon potency of the peptide or variant peptide is less than, or is about, W, wherein W is selected from 100, 75, 60, 50, 40, 30, 20, 15, 10, and 5. In some embodiments, the peptide or variant peptide exhibits at least 0.1% (e.g., about 0.5% or more, about 1% or more, about 5% or more, about 10% or more, or more) of the activity of native GLP-1 at the GLP-1 receptor (GLP-1 potency) and exhibits at least 0.1% (e.g., about 0.5% or more, about 1% or more, about 5% or more, about 10% or more, or more) of the activity of native glucagon at the glucagon receptor (glucagon potency).

Activity at the GIP Receptor

In addition to being active at the glucagon receptor and/or the GLP-1 receptor, the peptides and variant peptides described herein, in some aspects, exhibit low agonist activity at the GIP receptor. In such aspects, preferably such peptides and variant peptides are at least 100-fold selective for the GLP-1 receptor relative to the GIP receptor.

In other aspects, however, the peptide or variant peptide exhibits appreciable activity at the GIP receptor, e.g. the EC50 of the analog at the GIP receptor is less than about 50-fold different from its EC50 at the GLP-1 receptor, optionally, wherein the GIP potency of the analog is within about 50-fold of the GLP-1 potency of the analog. In exemplary embodiments, the peptides exhibit an EC50 for GIP receptor activation activity of about 1 µM or less, or 100 nM or less, or about 75, 50, 25, 10, 8, 6, 5, 4, 3, 2 or 1 nM or less. It is understood that a lower EC50 indicates higher activity or potency at the receptor. In some embodiments, the peptides and variant peptides described herein exhibit an EC50 at the GIP receptor that is about 0.001 nM, 0.01 nM, or 0.1 nM. In some embodiments, the peptides and variant peptides described herein exhibit an EC50 at the GIP receptor that is no more than about 100 nM. Receptor activation can be measured by in vitro assays measuring cAMP induction in HEK293 cells over-expressing the receptor, e.g. assaying HEK293 cells co-transfected with DNA encoding the receptor and a luciferase gene linked to cAMP responsive element as described in Example 2.

In some embodiments, the presently disclosed peptides and variant peptides exhibit at least about 0.1%, 1%, 10%, 50%, 100%, 150%, or 200% or higher activity at the GIP receptor relative to native GIP (GIP potency). In some embodiments, the peptides and variant peptides described herein exhibit no more than 1000%, 10,000%, 100,000%, or 1,000,000% activity at the GIP receptor relative to native GIP. A glucagon peptide's activity (potency) at a receptor relative to a native ligand of the receptor is calculated as the inverse ratio of EC50s for the peptide vs. the native ligand.

Thus, one aspect of the present disclosures provides peptides and variant peptides that exhibit activity at both the glucagon receptor and the GIP receptor ("glucagon/GIP co-agonists"). In some embodiments, the EC50 of the peptide at the GIP receptor is less than about 50-fold, 40-fold, 30-fold or 20-fold different (higher or lower) from its EC50 at the glucagon receptor. In some embodiments, the GIP potency of the peptide is less than about 500-, 450-, 400-, 350-, 300-, 250-, 200-, 150-, 100-, 75-, 50-, 25-, 20-, 15-, 10-, or 5-fold different (higher or lower) from its glucagon potency. In some embodiments, GLP-1 activity has been significantly reduced or destroyed, e.g., by an amino acid modification at position 7, a deletion of the amino acid(s)C-terminal to the amino acid at position 27 or 28, or a combination thereof.

In alternative aspects of the present disclosures, the peptides and variant peptides of the present disclosures exhibit activity at the GLP-1 and GIP receptors, but do not exhibit significant activity at the glucagon receptor ("GIP/GLP-1 co-agonists"), e.g., due to an amino acid modification of Gln at position 3. For example, substitution at this position with an acidic, basic, or a hydrophobic amino acid (glutamic acid, ornithine, norleucine) reduces glucagon activity. In other aspects, the peptides and variant peptides exhibit activity at each of the glucagon, GIP and GLP-1 receptors ("glucagon/GIP/GLP-1 tri-agonists"). For example, in either of these latter aspects, the EC50 of the peptide at the GIP receptor is less than about 50-fold, 40-fold, 30-fold or 20-fold different (higher or lower) from its EC50 at the GLP-1 receptor. In some embodiments, the GIP potency of the peptide is less than about 25-, 20-, 15-, 10-, or 5-fold different (higher or lower) from its GLP-1 potency. In some embodiments these peptides have about 10% or less of the activity of native glucagon at the glucagon receptor, e.g. about 1-10%, or about 0.1-10%, or greater than about 0.1% but less than about 10%.

Activity of Conjugates

In some embodiments, the peptides and variant peptides described herein exhibit activity or potency at the glucagon receptor and/or activity at the GLP-1 receptor and/or activity at the GIP receptor, as described above and, when the peptide or variant peptide is part of a conjugate (e.g., is conjugated to a heterologous moiety, e.g., a hydrophilic moiety, e.g., a polyethylene glycol), the peptide or variant peptide exhibits an activity that is lower (i.e. lower potency or higher EC50) than when the peptide or variant peptide is not part of the conjugate. In some aspects, the peptide or variant peptide when not part of conjugate exhibits a potency at the glucagon receptor and/or the GLP-1 receptor that is about 10-fold or greater than the potency of the peptide or variant peptide when part of a conjugate. In some aspects, the peptide or variant peptide when unconjugated exhibits an potency at the glucagon receptor and/or GLP-1 receptor that is about 10-fold, about 15-fold, about 20-fold, about 25-fold, about 30-fold, about 35-fold, about 40-fold, about 45-fold, about 50-fold, about 100-fold, or even greater-fold the potency of the peptide or variant peptide when conjugated.

Structure of the Glucagon Analogs

Acylation

In accordance with some embodiments, the glucagon analog comprises an acylated amino acid (e.g., a non-coded acylated amino acid (e.g., an amino acid comprising an acyl group which is non-native to a naturally-occurring amino acid)). The acylated amino acid in some embodiments causes the glucagon analog to have one or more of (i) a prolonged half-life in circulation, (ii) a delayed onset of action, (iii) an extended duration of action, (iv) an improved resistance to proteases, such as DPP-IV, and (v) increased potency at one or both of the GLP-1 and glucagon receptors. As shown herein, acylated glucagon analogs do not exhibit decreased activity at the glucagon and GLP-1 receptors in comparison to the corresponding unacylated glucagon analog. Rather, in some instances, acylated glucagon analogs actually exhibit increased activity at the GLP-1 and glucagon receptors. Accordingly, the potency of the acylated glucagon analogs is comparable to the unacylated versions of the glucagon analogs, if not enhanced.

In accordance with one embodiment, the glucagon analog comprises an acyl group which is attached to the glucagon analog via an ester, thioester, or amide linkage for purposes of prolonging half-life in circulation and/or delaying the onset of and/or extending the duration of action and/or improving resistance to proteases such as DPP-IV.

Acylation can be carried out at any position within the glucagon analog, including any of positions 1-29, a position C-terminal to the 29$^{th}$ amino acid (e.g., the amino acid at position 30, 31, 32, 33, 34, 35, 36, 37, 38, 39, 40, 41, 42, 43, 44, 45, 46, 47, etc., at a position within a C-terminal extension or at the C-terminus), provided that glucagon and/or GLP-1 activity is retained, if not enhanced. Nonlimiting examples include positions 5, 7, 10, 11, 12, 13, 14, 16, 17, 18, 19, 20, 21, 24, 27, 28, or 29. In exemplary embodiments, the glucagon analog comprises an acylated amino acid at one or more positions selected from the group consisting of: 9, 10, 12, 16, and 20. In exemplary embodiments, the glucagon analog comprises an acylated amino acid at one or more positions selected from the group consisting of: 10, 12, and 16. In exemplary embodiments, the glucagon analog comprises an acylated amino acid at one or more positions selected from the group consisting of: 9, 10, 12, 16, and 20. In exemplary embodiments, the glucagon analog comprises an acylated amino acid at one or more positions 10 and 12. In exemplary embodiments, the glucagon analog comprises an acylated amino acid at position 12. In exemplary embodiments, the glucagon analog comprises a C-terminal extension and an acylated amino acid at one or more positions selected from the group consisting of 9, 10, 12, 16, 20, and 37-43 (e.g., 40). In specific embodiments, acylation occurs at position 10 of the glucagon analog and the glucagon analog lacks an intramolecular bridge, e.g., a covalent intramolecular bridge (e.g., a lactam bridge). Such acylated glucagon analogs lacking an intramolecular bridge demonstrate enhanced activity at the GLP-1 and glucagon receptors as compared to the corresponding non-acylated analogs lacking a covalent intramolecular bridge and in comparison to the corresponding analogs lacking an intramolecular bridge acylated at a position other than position 10. As shown herein, acylation at position 10 can even transform a glucagon analog having little activity at the glucagon receptor to a glucagon analog having activity at both the glucagon and GLP-1 receptors. Accordingly, the position at which acylation occurs can alter the overall activity profile of the glucagon analog.

The glucagon analog in some embodiments are acylated at the same amino acid position where a hydrophilic moiety is linked, or at a different amino acid position. Nonlimiting examples include acylation at position 10 and pegylation at one or more positions in the C-terminal portion of the glucagon analog, e.g., position 24, 28 or 29, within a C-terminal extension, or at the C-terminus (e.g., through adding a C-terminal Cys).

The acyl group can be covalently linked directly to an amino acid of the glucagon analog, or indirectly to an amino acid of the glucagon analog via a spacer, wherein the spacer is positioned between the amino acid of the glucagon analog and the acyl group.

In specific aspects, the glucagon analog is modified to comprise an acyl group by direct acylation of an amine, hydroxyl, or thiol of a side chain of an amino acid of the glucagon analog. In some embodiments, acylation is at position 10, 20, 24, or 29 of the glucagon analog. In this regard, the acylated glucagon analog can comprise the amino acid sequence of SEQ ID NO: 1, or a modified amino acid sequence thereof comprising one or more of the amino acid modifications described herein, with at least one of the amino acids at positions 10, 20, 24, and 29 of the analog modified to any amino acid comprising a side chain amine, hydroxyl, or thiol. In some specific embodiments, the direct acylation of the glucagon analog occurs through the side chain amine, hydroxyl, or thiol of the amino acid at position 10.

In some embodiments, the amino acid comprising a side chain amine is an amino acid of Formula I:

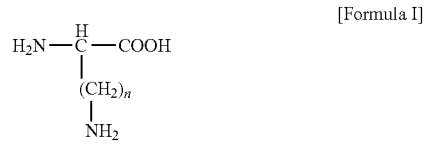

[Formula I]

wherein n = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

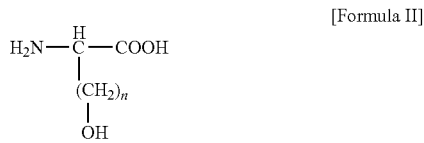

[Formula II]

wherein n = 1 to 4

In some exemplary embodiments, the amino acid of Formula II is the amino acid wherein n is 1 (Ser).

In yet other embodiments, the amino acid comprising a side chain thiol is an amino acid of Formula III:

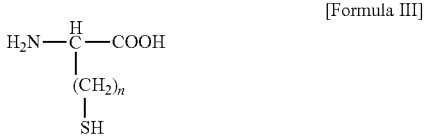

[Formula III]

wherein n = 1 to 4

In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments, the acylated glucagon comprises a spacer between the analog and the acyl group. In some embodiments, the glucagon analog is covalently bound to the spacer, which is covalently bound to the acyl group.

In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COOH (e.g., Lys, Orn, Ser, Asp, or Glu) is suitable. In this respect, the acylated glucagon analog can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp, Glu, homoglutamic acid, homocysteic acid, cysteic acid, gamma-glutamic acid.

In the instance in which the side chain amine of the amino acid of the spacer is acylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be acylated, such that the glucagon analog is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C12 to C18 fatty acyl group, e.g., C14 fatty acyl group, C16 fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms.

In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methyl-alanine (Me-Ala), aminobutyric acid (Abu), γ-aminobutyric acid (7-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (Me-Phe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (MeVal), and alkylated 3-mercaptopropionic acid.

In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, Glu-Glu, and γ-Glu-γ-Glu.

In some exemplary embodiments, the glucagon analog is modified to comprise an acyl group by acylation of an amine, hydroxyl, or thiol of a spacer, which spacer is attached to a side chain of an amino acid at position 10, 20, 24, or 29, or at the C-terminal amino acid of the glucagon analog.

In yet more specific embodiments, the acyl group is attached to the amino acid at position 10 of the glucagon analog and the length of the spacer and acyl group is 14 to 28 atoms. The amino acid at position 10, in some aspects, is an amino acid of Formula I, e.g., Lys, or a disubstituted amino acid related to Formula I. In more specific embodiments, the glucagon analog lacks an intramolecular bridge, e.g., a covalent intramolecular bridge. The glucagon analog, for example, can be a glucagon analog comprising one or more alpha, alpha-disubstituted amino acids, e.g., AIB, for stabilizing the alpha helix of the analog.

Suitable methods of peptide acylation via amines, hydroxyls, and thiols are known in the art. See, for example, Example 19 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated amino acid can be of any size, e.g., any length carbon chain, and can be linear or branched. In some specific embodiments, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In some embodiments, the glucagon analog comprises an acylated amino acid by acylation of a long chain alkane by the glucagon analog. In specific aspects, the long chain alkane comprises an amine, hydroxyl, or thiol group (e.g., octadecylamine, tetradecanol, and hexadecanethiol) which reacts with a carboxyl group, or activated form thereof, of the glucagon analog. The carboxyl group, or activated form thereof, of the glucagon analog can be part of a side chain of an amino acid (e.g., glutamic acid, aspartic acid) of the glucagon analog or can be part of the analog backbone.

In certain embodiments, the glucagon analog is modified to comprise an acyl group by acylation of the long chain alkane by a spacer which is attached to the glucagon analog. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form of a carboxyl group" refers to a carboxyl group with the general formula R(C=O)X, wherein X is a leaving group and R is the glucagon analog or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects, in which a long chain alkane is acylated by the glucagon analog or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, an amine, hydroxyl, or thiol group of the glucagon analog is acylated with a cholesterol acid. In a specific embodiment, the glucagon analog is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the glucagon analog comprises the structure:

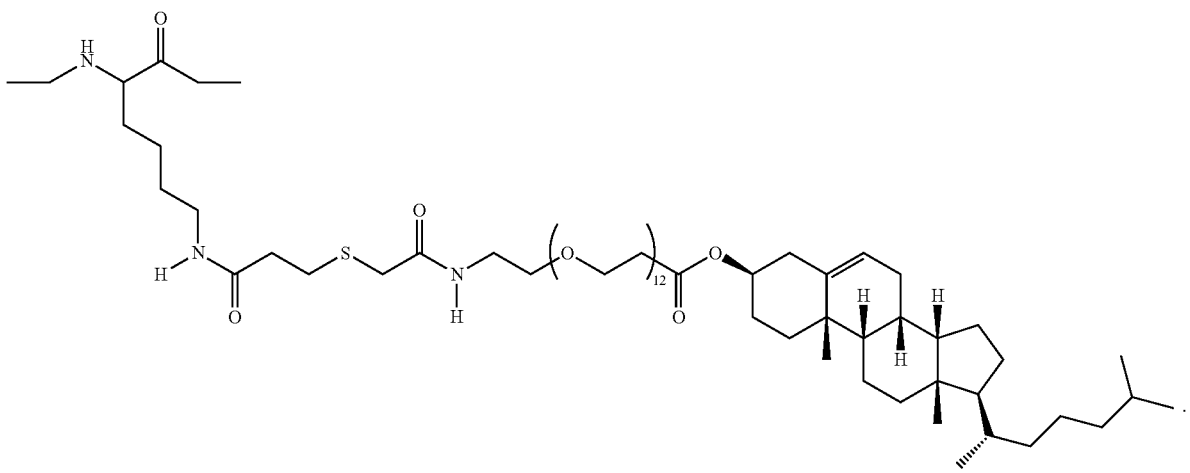

The acylated glucagon analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon analog can comprise SEQ ID NO: 1, including any of the modifications described herein, in which at least one of the amino acids at position 10, 20, 24, and 29 of the analog comprises an acyl group and at least one of the amino acids at position 16, 17, 21, 24, or 29, a position within a C-terminal extension, or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the acyl group is attached to position 10, optionally via a spacer comprising Cys, Lys, Orn, homo-Cys, or Ac-Phe, and the hydrophilic moiety is incorporated at a Cys residue at position 24.

Alternatively, the acylated glucagon analog can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation

In accordance with some embodiments, the glucagon analog comprises an alkylated amino acid (e.g., a non-coded alkylated amino acid (e.g., an amino acid comprising an alkyl group which is non-native to a naturally-occurring amino acid)). Without being held to any particular theory, it is believed that alkylation of glucagon analogs achieve similar, if not the same, effects as acylation of the glucagon analogs, e.g., a prolonged half-life in circulation, a delayed onset of action, an extended duration of action, an improved resistance to proteases, such as DPP-IV, and increased potency at the GLP-1 and glucagon receptors.

Alkylation can be carried out at any positions within the glucagon analog, including any of the positions described herein as a site for acylation, including but not limited to, any of amino acid positions 1-29, an amino acid position C-terminal to the 29$^{th}$ residue, e.g., 30, 31, 32, 33, 34, 35, 36, 37, 38, 39, 40, 41, 42, 43, 44, 45, 46, 47, etc., at a position within a C-terminal extension, or at the C-terminus, provided that the glucagon activity or GLP-1 activity is retained. Nonlimiting examples include positions 5, 7, 10, 11, 12, 13, 14, 16, 17, 18, 19, 20, 21, 24, 27, 28, or 29. In exemplary embodiments, the glucagon analog comprises an alkylated amino acid at one or more positions selected from the group consisting of: 9, 10, 12, 16, and 20. In exemplary embodiments, the glucagon analog comprises an alkylated amino acid at one or more positions selected from the group consisting of: 10, 12, and 16. In exemplary embodiments, the glucagon analog comprises an alkylated amino acid at one or more positions selected from the group consisting of: 9, 10, 12, 16, and 20. In exemplary embodiments, the glucagon analog comprises an alkylated amino acid at one or more positions 10 and 12. In exemplary embodiments, the glucagon analog comprises an alkylated amino acid at position 12. In exemplary embodiments, the glucagon analog comprises a C-terminal extension and an alkylated amino acid at one or more positions selected from the group consisting of 9, 10, 12, 16, 20, and 37-43 (e.g., 40). The alkyl group can be covalently linked directly to an amino acid of the glucagon analog, or indirectly to an amino acid of the glucagon analog via a spacer, wherein the spacer is positioned between the amino acid of the glucagon analog and the alkyl group. Glucagon analog may be alkylated at the same amino acid position where a hydrophilic moiety is linked, or at a different amino acid position. Nonlimiting examples include alkylation at position 10 and pegylation at one or more positions in the C-terminal portion of the glucagon analog, e.g., position 24, 28 or 29, within a C-terminal extension, or at the C-terminus (e.g., through adding a C-terminal Cys).

In specific aspects, the glucagon analog is modified to comprise an alkyl group by direct alkylation of an amine, hydroxyl, or thiol of a side chain of an amino acid of the glucagon analog. In some embodiments, alkylation is at position 10, 20, 24, or 29 of the glucagon analog. In this regard, the alkylated glucagon analog can comprise the amino acid sequence of SEQ ID NO: 2, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments, the direct alkylation of the glucagon analog occurs through the side chain amine, hydroxyl, or thiol of the amino acid at position 10.

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula II is the amino acid wherein n is 1 (Ser).

In yet other embodiments, the amino acid comprising a side chain thiol is an amino acid of Formula III. In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments, the alkylated glucagon analog comprises a spacer between the analog and the alkyl group. In some embodiments, the glucagon analog is covalently bound to the spacer, which is covalently bound to the alkyl group. In some exemplary embodiments, the glucagon analog is modified to comprise an alkyl group by alkylation of an amine, hydroxyl, or thiol of a spacer, which spacer is attached to a side chain of an amino acid at position 10, 20, 24, or 29 of the glucagon analog. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon analog can comprise a modified amino acid sequence of SEQ ID NO: 1, comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the glucagon analog is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser.

When alkylation occurs through a thiol group of spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer is comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydropholic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a C12 to C18 alkyl group, e.g., C14 alkyl group, C16 alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl is 17 to 28 (e.g., 19 to 26, 19 to 21) atoms.

In accordance with certain foregoing embodiments, the bifunctional spacer can be a synthetic or non-naturally occurring or non-coded amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer can be composed of naturally-occurring or coded and/or non-coded or non-naturally occurring amino acids, including, for example, any of the amino acids taught herein. In some embodiments, the spacer comprises an overall negative charge, e.g., comprises one or two negative-charged amino acids. In some embodiments, the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

Suitable methods of peptide alkylation via amines, hydroxyls, and thiols are known in the art. For example, a Williamson ether synthesis can be used to form an ether linkage between a hydroxyl group of the glucagon analog and the alkyl group. Also, a nucleophilic substitution reaction of the peptide with an alkyl halide can result in any of an ether, thioether, or amino linkage.

The alkyl group of the alkylated glucagon analog can be of any size, e.g., any length carbon chain, and can be linear or branched. In some embodiments, the alkyl group is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments of the disclosure, the glucagon analog comprises an alkylated amino acid by reacting a nucleophilic, long chain alkane with the glucagon analog, wherein the glucagon analog comprises a leaving group suitable for nucleophilic substitution. In specific aspects, the nucleophilic group of the long chain alkane comprises an amine, hydroxyl, or thiol group (e.g., octadecylamine, tetradecanol, and hexadecanethiol). The leaving group of the glucagon analog can be part of a side chain of an amino acid or can be part of the peptide backbone. Suitable leaving groups include, for example, N-hydroxysuccinimide, halogens, and sulfonate esters.

In certain embodiments, the glucagon analog is modified to comprise an alkyl group by reacting the nucleophilic, long chain alkane with a spacer which is attached to the glucagon analog, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

With regard to these aspects of the disclosure, in which a long chain alkane is alkylated by the glucagon analog or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, alkylation can occur between the glucagon analog and a cholesterol moiety. For example, the hydroxyl group of cholesterol can displace a leaving group on the long chain alkane to form a cholesterol-glucagon analog product.

The alkylated glucagon analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon analog can comprise a modified SEQ ID NO: 1 comprising one or more of the amino acid modifications described herein, in which at least one of the amino acids at position 10, 20, 24, and 29 comprise an alkyl group and at least one of the amino acids at position 16, 17, 21, 24, and 29, a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10, optionally via a spacer comprising Cys, Lys, Orn, homo-Cys, or Ac-Phe, and the hydrophilic moiety is incorporated at a Cys residue at position 24.

Alternatively, the alkylated glucagon analog can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Stabilization of the Alpha Helix and Alpha Helix Promoting Amino Acids

Without being bound to any particular theory, the glucagon analogs described herein comprise a helical structure, e.g., an alpha helix. In some embodiments, the glucagon analog comprises amino acids which stabilize the alpha helical structure. Accordingly, in some aspects, the glucagon analog comprises one or more alpha helix promoting amino acids. As used herein, the term "alpha helix promoting amino acid" refers to an amino acid which provides increased stability to an alpha helix of the glucagon analog of which it is a part. Alpha helix promoting amino acids are known in the art. See, for example, Lyu et al., *Proc Natl Acad Sci U.S.A.* 88: 5317-5320 (1991); Branden & Tooze, *Introduction to Protein Structure*, Garland Publishing, New York, N.Y., 1991; Fasman, *Prediction of Protein Structure and the Principles of Protein Conformation*, ed. Fasman, Plenum, N.Y., 1989). Suitable alpha helix promoting amino acids for purposes herein include, but are not limited to: alanine, norvaline, norleucine, alpha aminobutyric acid, alpha-aminoisobutyric acid, leucine, isoleucine, valine, and the like. In some embodiments, the alpha helix promoting amino acid is any amino acid which is part of an alpha helix found in a naturally-occurring protein, e.g., Leu, Phe, Ala, Met, Gly, Ile, Ser, Asn, Glu, Asp, Lys, Arg.

In some embodiments, the alpha helix promoting amino acid provides more stability to the alpha helix as compared to glycine or alanine. In some embodiments, the alpha helix promoting amino acid is an alpha, alpha di-substituted amino acid.

Alpha Helix: Position of Alpha Helix Promoting Amino Acids

In some embodiments, the glucagon analog comprises an amino acid sequence which is similar to native glucagon (SEQ ID NO: 1) and the glucagon analog comprises at least one alpha helix promoting amino acid. In some embodiments, the alpha helix promoting amino acid is located at any of positions 12 to 29 (according to the numbering of native glucagon (SEQ ID NO: 1). In some embodiments, the glucagon analog comprises a modified amino acid sequence of SEQ ID NO: 1 and comprises at least one alpha helix promoting amino acid, e.g., at one or more of positions 12, 13, 14, 15, 16, 17, 18, 19, 20, 21, 22, 23, 24, 25, 26, 27, 28, 29. In some embodiments, the glucagon analog comprises an alpha helix promoting amino acid at one, two, three, or all of positions 16, 17, 20, and 21.

Alpha Helix: Alpha, Alpha Di-Substituted Amino Acids

In some embodiments, the alpha helix promoting amino acid is an alpha,alpha di-substituted amino acid. In specific embodiments, the alpha, alpha di-substituted amino acid comprises $R^1$ and $R^2$, each of which is bonded to the alpha carbon, wherein each of $R^1$ and $R^2$ is independently selected from the group consisting of C1-C4 alkyl, optionally substituted with a hydroxyl, amide, thiol, halo, or $R^1$ and $R^2$ together with the alpha carbon to which they are attached form a ring (e.g., a C3-C8 ring). In some embodiments, each of $R^1$ and $R^2$ is selected from the group consisting of: methyl, ethyl, propyl, and n-butyl, or $R^1$ and $R^2$ together form a cyclooctane or cycloheptane (e.g., 1-aminocyclooctane-1-carboxylic acid). In some embodiments, $R^1$ and $R^2$ are the same. In some embodiments, $R^1$ is different from $R^2$. In certain aspects, each of $R^1$ and $R^2$ is a C1-C4 alkyl. In some aspects, each of $R^1$ and $R^2$ is a C1 or C2 alkyl. In some embodiments, each of $R^1$ and $R^2$ is methyl, such that the alpha, alpha disubstituted amino acid is alpha-aminoisobutyric acid (AIB).

In some aspects, the glucagon analogs described herein comprises one or more alpha, alpha di-substituted amino acids and the glucagon analogs specifically lack a covalent intramolecular bridge (e.g., a lactam), since the alpha, alpha disubstituted amino acid is capable of stabilizing the alpha helix in the absence of a covalent bridge. In some aspects, the glucagon analog comprises one or more alpha, alpha di-substituted amino acids at the C-terminus (around positions 12-29). In some embodiments, one, two, three, four or more of positions 16, 17, 18, 19, 20, 21, 24, 28, or 29 of the glucagon analog is substituted with an α,α-disubstituted amino acid, e.g., amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). For example, substitution of position 16 with AIB enhances GLP-1 activity, in the absence of an intramolecular bridge, e.g., a non-covalent intramolecular bridge (e.g., a salt bridge) or a covalent intramolecular bridge (e.g., a lactam). In some embodiments, one, two, three or more of positions 16, 20, 21 or 24 are substituted with AIB. In specific embodiments, one or both of the amino acids corresponding to positions 2, 16, of native human glucagon (SEQ ID NO: 1) are substituted with an alpha, alpha disubstituted amino acid such as AIB.

In accordance with some embodiments, the glucagon analog lacking an intramolecular bridge comprises one or more substitutions within amino acid positions 12-29 with an α,α-disubstituted amino acid and an acyl or alkyl group covalently attached to the side chain of the amino acid at position 10 of the glucagon analog. In specific embodiments, the acyl or alkyl group is not naturally occurring on an amino acid. In certain aspects, the acyl or alkyl group is non-native to the amino acid at position 10. Such acylated or alkylated glucagon peptides lacking an intramolecular bridge exhibit enhanced activity at the GLP-1 and glucagon receptors as compared to the non-acylated counterpart peptides. Further enhancement in activity at the GLP-1 and glucagon receptors can be achieved by the acylated glucagon peptides lacking an intramolecular bridge by incorporating a spacer between the acyl or alkyl group and the side chain of the amino acid at position 10 of the analog. Acylation and alkylation, with or without incorporating spacers, are further described herein.

Alpha Helix: Intramolecular Bridges

In some embodiments, the alpha helix promoting amino acid is an amino acid which is linked to another amino acid of the glucagon analog via an intramolecular bridge. In such embodiments, each of these two amino acids linked via an intramolecular bridge is considered an alpha helix promoting amino acid. In some embodiments, the glucagon analog comprises one or two intramolecular bridges. In some specific embodiments, the glucagon analog comprises one intramolecular bridge in combination with at least one other alpha helix promoting amino acid, e.g., an alpha, alpha-disubstituted amino acid.

In some embodiments, the intramolecular bridge is a bridge which connects two parts of the glucagon analog via noncovalent bonds, including, for example, van der Waals interactions, hydrogen bonds, ionic bonds, hydrophobic interactions, dipole-dipole interactions, and the like. In this regard, the glucagon analog in certain aspects comprises a non-covalent intramolecular bridge. In some embodiments, the non-covalent intramolecular bridge is a salt bridge.

In some embodiments, the intramolecular bridge is a bridge which connects two parts of the analog via covalent bonds. In this regard, the glucagon analog in certain aspects comprises a covalent intramolecular bridge.

In some embodiments, the intramolecular bridge (e.g., non-covalent intramolecular bridge, covalent intramolecular bridge) is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25). More particularly, the side chains of the amino acid pairs 12 and 16, 16 and 20, 20 and 24 or 24 and 28 (amino acid pairs in which i=12, 16, 20, or 24) are linked to one another and thus stabilize the glucagon alpha helix. Alternatively, i can be 17. In some specific embodiments, the glucagon analog comprises an intramolecular bridge between amino acids 17 and 21. In some specific embodiments, the glucagon analog comprises an intramolecular bridge between the amino acids at positions 16 and 20 or 12 and 16 and a second intramolecular bridge between the amino acids at positions 17 and 21. Glucagon analogs comprising one or more intramolecular bridges are contemplated herein. In specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26). In some specific embodiments, j is 17. In specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22). In some specific embodiments, k is 12, 13, or 17. In an exemplary embodiment, k is 17.

Alpha Helix: Amino Acids Involved in Intramolecular Bridges

Examples of amino acid pairings that are capable of bonding (covalently or non-covalently) to form a six-atom linking bridge include Orn and Asp, Glu and an amino acid of Formula I, wherein n is 2, and homoglutamic acid and an amino acid of Formula I, wherein n is 1, wherein Formula I is:

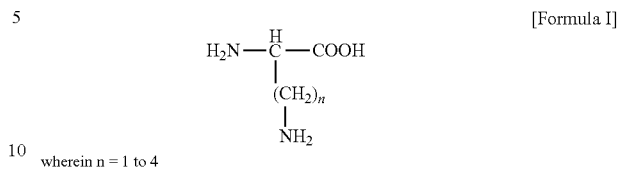

wherein n = 1 to 4

Examples of amino acid pairings that are capable of bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect.

Even without covalent linkage, the amino acid pairings described above (or similar pairings that one of ordinary skill in the art can envision) may also provide added stability to the alpha-helix through non-covalent bonds, for example, through formation of salt bridges or hydrogen-bonding interactions. Accordingly, salt bridges may be formed between: Orn and Glu; Lys and Asp; Homo-serine and Homo-glutamate; Lys and Glu; Asp and Arg; Homo-Lys and Asp; Orn and Homo-Glutamate; 4-aminoPhe and Asp; Tyr and Asp; Homo-Lys and Glu; Lys and Homo-Glu; 4-aminoPhe and Glu; or Tyr and Glu. In some embodiments, the analog comprises a salt bridge between any of the following pairs of amino acids: Orn and Glu; Lys and Asp; Lys and Glu; Asp and Arg; Homo-Lys and Asp; Orn and Homo-Glutamate; Homo-Lys and Glu; and Lys and Homo-Glu. Salt bridges may be formed between other pairs of oppositely charged side chains. See, e.g., Kallenbach et al., *Role of the Peptide Bond in Protein Structure and Folding*, in The Amide Linkage: Structural Significance in Chemistry, Biochemistry, and Materials Science, John Wiley & Sons, Inc. (2000).

In some embodiments, the non-covalent intramolecular bridge is a hydrophobic bridge. In accordance with one embodiment, the alpha helix of the analog is stabilized through the incorporation of hydrophobic amino acids at positions j and j+3 or i and i+4. For instance, i can be Tyr and i+4 can be either Val or Leu; i can be Phe and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position. It should also be understood that suitable amino acid pairings can be formed for j and j+3.

Alpha Helix: Covalent Intramolecular Bridge

In some embodiments, the covalent intramolecular bridge is a lactam ring or lactam bridge. The size of the lactam ring can vary depending on the length of the amino acid side chains, and in one embodiment the lactam is formed by linking the side chains of an ornithine to a aspartic acid side chain. Lactam bridges and methods of making the same are known in the art. See, for example, Houston, Jr., et al., *J Peptide Sci* 1: 274-282 (2004), and Example 1 herein. In some embodiments, the analog comprises a modified sequence of SEQ ID NO: 1 and a lactam bridge between i and i+4, wherein i is as defined herein above. In some embodiments, the glucagon analog comprises two lactam bridges: one between the amino acids at positions 16 and 20 and another between the amino acids at positions 17 and 21. In some embodiments, the glucagon analog comprises one lactam bridge and one salt bridge. Further exemplary embodiments, are described herein in the section entitled "EXAMPLES." Further exemplary embodiments include the following pairings, optionally with a lactam bridge: Glu at position 12 with Lys at position 16; native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28.

In some embodiments, the covalent intramolecular bridge is a lactone. Suitable methods of making a lactone bridge are known in the art. See, for example, Sheehan et al., *J Am Chem Soc* 95: 875-879 (1973).

In some aspects, olefin metathesis is used to cross-link one or two turns of the alpha helix of the analog using an all-hydrocarbon cross-linking system. The glucagon analog in this instance comprises α-methylated amino acids bearing olefinic side chains of varying length and configured with either R or S stereochemistry at the j and j+3 or i and i+4 positions. In some embodiments, the olefinic side comprises $(CH_2)n$, wherein n is any integer between 1 to 6. In some embodiments, n is 3 for a cross-link length of 8 atoms. In some embodiments, n is 2 for a cross-link length of 6 atoms. An exemplary glucagon analog comprising an olefinic cross-link is described herein as SEQ ID NO: 17. Suitable methods of forming such intramolecular bridges are described in the art. See, for example, Schafmeister et al., *J. Am. Chem. Soc.* 122: 5891-5892 (2000) and Walensky et al., *Science* 305: 1466-1470 (2004). In alternative embodiments, the analog comprises O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In specific aspects, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α,ω-diaminoalkane tethers, e.g., 1,4-diaminopropane and 1,5-diaminopentane) between two Glu residues at positions i and i+7 are used to stabilize the alpha helix of the analog. Such tethers lead to the formation of a bridge 9-atoms or more in length, depending on the length of the diaminoalkane tether. Suitable methods of producing peptides cross-linked with such tethers are described in the art. See, for example, Phelan et al., *J. Am. Chem. Soc.* 119: 455-460 (1997).

In yet other embodiments, a disulfide bridge is used to cross-link one or two turns of the alpha helix of the analog. Alternatively, a modified disulfide bridge in which one or both sulfur atoms are replaced by a methylene group resulting in an isosteric macrocyclization is used to stabilize the alpha helix of the analog. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet other embodiments, the alpha helix of the analog is stabilized via the binding of metal atom by two His residues or a His and Cys pair positioned at j and j+3, or i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the analog can alternatively be stabilized through other means of peptide cyclizing, which means are reviewed in Davies, J. Peptide. Sci. 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

DPP-IV Resistant Peptides

In some embodiments, the glucagon analog comprises at position 1 or 2, or at both positions 1 and 2, an amino acid which achieves resistance of the glucagon analog to dipeptidyl peptidase IV (DPP IV) cleavage. In some embodiments, the glucagon analog comprises at position 1 an aminio acid selected from the group consisting of: D-histidine, desamino-histidine, hydroxyl-histidine, acetyl-histidine, homo-histidine, N-methyl histidine, alpha-methyl histidine, imidazole acetic acid, or alpha, alpha-dimethyl imidiazole acetic acid (DMIA). In some embodiments, the glucagon analog comprises at position 2 an amino acid selected from the group consisting of: D-serine, D-alanine, valine, glycine, N-methyl serine, N-methyl alanine, or alpha, aminoisobutyric acid. In some embodiments, the glucagon analog comprises at position 2 an amino acid which achieves resistance of the glucagon analog to DPP IV and the amino acid which achieves resistance of the glucagon analog to DPP IV is not D-serine.

In some aspects, the glucagon analog comprising an amino acid which achieves resistance of the glucagon analog to DPP IV further comprises an amino acid modification which stabilizes the alpha helix found in the C-terminal portion of glucagon, e.g., through a covalent bond between amino acids at positions "i" and "i+4", e.g., 12 and 16, 16 and 20, or 20 and 24. In some embodiments, this covalent bond is a lactam bridge between a glutamic acid at position 16 and a lysine at position 20. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

Modification of Position 1

In some specific embodiments, the glucagon analog comprises (a) an amino acid substitution of His at position 1 with a large, aromatic amino acid and (b) an intramolecular bridge that stabilizes that alpha-helix in the C-terminal portion of the molecule (e.g., around positions 12-29). In specific embodiments, the amino acid at position 1 is replaced with Tyr, Phe, Trp, amino-Phe, nitro-Phe, chloro-Phe, sulfo-Phe, 4-pyridyl-Ala, methyl-Tyr, or 3-amino Tyr. The intramolecular bridge, in some embodiments, is any of those described herein. In some aspects, the intramolecular bridge is between the side chains of two amino acids that are separated by three intervening amino acids, i.e., between the side chains of amino acids i and i+4. In some embodiments, the intramolecular bridge is a lactam bridge. In some embodiments, the glucagon analog comprises a large, aromatic amino acid at position 1 and a lactam bridge between the amino acids at positions 16 and 20 of the analog. Such a glucagon analog in some aspects further comprises one or more (e.g., two, three, four, five or more) of the other modifications described herein. For example, the glucagon analog can comprise an amide in place of the C-terminal carboxylate. Also, in some embodiments, such glucagon analogs further comprise one or more of a large aliphatic amino acid at position 17, an imidazole containing amino acid at position 18, and a positive-charged amino acid at position 19. In some embodiments, the glucagon analogs comprising a modification at position 1 and an intramolecular bridge further comprises the amino acid sequence Ile-His-Gln at positions 17-19. Such modifications can be made without destroying activity of the glucagon analog at the GLP-1 receptor and the glucagon receptor. In some embodiments, the glucagon analog additionally comprises an acylated or alkylated amino acid residue.

Modification of Position 3

In some embodiments, the third amino acid of SEQ ID NO: 1 (Gln3) is substituted with an acidic, basic, or hydrophobic amino acid residue and such modification causes the glucagon receptor activity to be reduced. In some embodiments, the acidic, basic, or hydrophobic amino acid is glutamic acid, ornithine, norleucine. In some aspects, modification with one of these residues has led the glucagon analog to exhibit a substantially reduced or destroyed glucagon receptor activity. The glucagon analogs that are substituted with, for example, glutamic acid, ornithine, or norleucine in some aspects have about 10% or less of the activity of native glucagon at the glucagon receptor, e.g., about 1-10%, or about 0.1-10%, or greater than about 0.1% but less than about 10%, while exhibiting at least 20% of the activity of GLP-1 at the GLP-1 receptor. In some embodiments, the glucagon analogs exhibit about 0.5%, about 1% or about 7% of the activity of native glucagon, while exhibiting at least 20% of the activity of GLP-1 at the GLP-1 receptor.

In some embodiments, the glutamine at position 3 of SEQ ID NO: 1 of the glucagon analog is substituted with a glutamine analog without a substantial loss of activity at the glucagon receptor, and in some cases, with an enhancement of glucagon receptor activity. In some embodiments, the glutamine analog is a naturally occurring or a non-naturally occurring or non-coded amino acid comprising a side chain of Structure I, II or III:

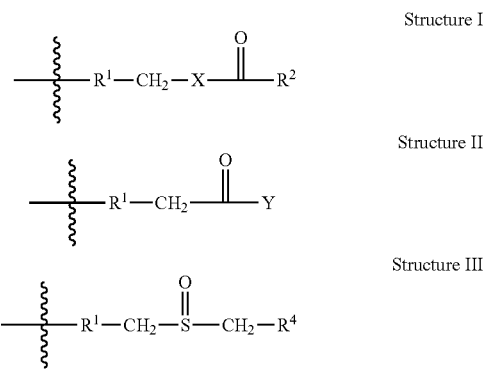

wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R^1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl. In exemplary embodiments, an amino acid comprising a side chain of Structure I is provided where, $R^1$ is $CH_2$—S, X is NH, and $R^2$ is $CH_3$ (acetamidomethyl-cysteine, C(Acm)); $R^1$ is $CH_2$, X is NH, and $R^2$ is $CH_3$ (acetyldiaminobutanoic acid, Dab(Ac)); $R^1$ is $C_o$ alkyl, X is NH, $R^2$ is $NHR^4$, and $R^4$ is H (carbamoyl-diaminopropanoic acid, Dap(urea)); or $R^1$ is $CH_2$—$CH_2$, X is NH, and $R^2$ is $CH_3$ (acetylornithine, Orn(Ac)). In exemplary embodiments, an amino acid comprising a side chain of Structure II is provide where, $R^1$ is $CH_2$, Y is $NHR^4$, and $R^4$ is $CH_3$ (methylglutamine, Q(Me)); In exemplary embodiments, an amino acid comprising a side chain of Structure III is provided where, $R^1$ is $CH_2$ and $R^4$ is H (methionine-sulfoxide, M(O)); In specific embodiments, the amino acid at position 3 is substituted with Dab(Ac) For example, glucagon agonists can comprise a modified amino acid sequence of SEQ ID NO: 595, SEQ ID NO: 601 SEQ ID NO: 603, SEQ ID NO: 604, SEQ ID NO: 605, and SEQ ID NO: 606 of the sequence listing of International Patent Application No. PCT/US2009/047438, filed on Jun. 16, 2009, which is incorporated by reference in its entirety, wherein these amino acid sequences are modified as further described herein, e.g., modified to comprise at least three alpha helix promoting amino acids, modified to comprise (i) an acylated or alkylated amino acid at position 10, (ii) an alpha helix promoting amino acid at position 16, (iii) an aliphatic amino acid at position 17 and/or 18, and (iv) at least one charged amino acid located C-terminal to position 27, and, optionally, further modifications; modified to comprise at least three amino acids of the amino acids 18-24 of Exendin-4 (SEQ ID NO: 8) at the corresponding positions of the glucaogon analog.

Modification of Position 7

In some embodiments, the glucagon analog comprises a modified SEQ ID NO: 1 with an amino acid modification at position 7. In some aspects, the amino acid at position 7 of SEQ ID NO: 1 (Thr) is substituted with a large, aliphatic amino acid, e.g., Ile, Leu, Ala, and the like. Such modifications are believed to drastically reduce activity at the GLP-1 receptor of the glucagon analog.

Modification of Position 15

In some embodiments, the glucagon analogs comprise a modified SEQ ID NO: 1 with an amino acid modification at position 15 which improves stability. In some aspects, the amino acid at position 15 of SEQ ID NO: 1 is deleted or substituted with glutamic acid, homoglutamic acid, cysteic acid or homocysteic acid. Such modifications reduce degradation or cleavage of the analog over time, especially in acidic or alkaline buffers, e.g., buffers at a pH within the range of 5.5 to 8. In some embodiments, the glucagon analogs comprising this modification retains at least 75%, 80%, 90%, 95%, 96%, 97%, 98% or 99% of the original analog after 24 hours at 25° C.

Modification of Position 16

In accordance with one embodiment, analogs of glucagon are provided that have enhanced potency and optionally improved solubility and stability. In one embodiment, enhanced glucagon and GLP-1 potency is provided by an amino acid modification at position 16 of native glucagon (SEQ ID NO: 1). By way of nonlimiting example, such enhanced potency can be provided by substituting the naturally occurring serine at position 16 with glutamic acid or with another negative-charged amino acid having a side chain with a length of 4 atoms, or alternatively with any one of glutamine, homoglutamic acid, or homocysteic acid, or a charged amino acid having a side chain containing at least one heteroatom, (e.g., N, O, S, P) and with a side chain length of about 4 (or 3-5) atoms. In some embodiments, the glucagon analog comprises a modified SEQ ID NO: 1 comprising a substitution of the Ser at position 16 with an amino acid selected from the group consisting of glutamic acid, glutamine, homoglutamic acid, homocysteic acid, threonine or glycine. In some aspects, the serine residue at position 16 is substituted with an amino acid selected from the group consisting of glutamic acid, glutamine, homoglutamic acid and homocysteic acid. In some specific aspects, the serine residue at position 16 is substituted with glutamic acid or a conservative substitution thereof (e.g. an Exendin-4 amino acid).

In alternative embodiments, the glucagon analog comprises a modified sequence of SEQ ID NO: 1 modified by a substitution of Ser at position 16 with Thr or AIB or another alpha helix promoting amino acid as described above. In some embodiments, the alpha helix promoting amino acid forms a non-covalent intramolecular bridge with an amino acid at j+3 or i+4.

Modification at Positions 17-18

In some embodiments, the glucagon analog comprises a modified SEQ ID NO: 1 in which the dibasic Arg-Arg site at positions 17 and 18 is eliminated. Without being bound to any particular theory, it is believed that elimination of the dibasic site in some embodiments improves the in vivo efficacy of the glucagon analog. In some aspects, the glucagon analog is modified in this regard by substituting one or both of the amino acids at positions 17 and 18 of SEQ ID NO: 1 with an amino acid which is not basic, e.g., with an aliphatic amino acid. In some embodiments, one of the amino acids at position 17 or 18 is deleted or an amino acid is inserted in between positions 17 and 18. In some embodiments, the Arg at position 17 is substituted with another amino acid as described herein, e.g., Gln, an amino acid comprising a hydrophilic moiety, an alpha helix promoting amino acid. In some embodiments, the alpha helix promoting amino acid forms a non-covalent intramolecular bridge with an amino acid at j+3 or i+4. In some embodiments, the Arg at position 18 is substituted with another amino acid as described herein. In exemplary aspects, the amino acid at position 18 is an alpha, alpha, disubstituted amino acid, e.g., AIB. In some aspects, the amino acid at position 18 is a small aliphatic amino acid, e.g., Ala. In some specific aspects, the amino acid at position 18 is a small aliphatic amino acid, e.g., Ala, and the Arg at position 17 remains unmodified.

Modification of Position 20

Enhanced activity at the GLP-1 receptor is also provided by an amino acid modification at position 20. In some embodiments, the glutamine at position 20 is replaced with an alpha helix promoting amino acid, e.g. AIB, as described above. In some embodiments, the alpha helix promoting amino acid forms a non-covalent intramolecular bridge with an amino acid at j–3 or i–4. In some specific embodiments the amino acid is a hydrophilic amino acid having a side chain that is either charged or has an ability to hydrogen-bond, and is at least about 5 (or about 4-6) atoms in length, for example, lysine, citrulline, arginine, or ornithine, and optionally forms a salt bridge with another alpha helix promiting amino acid at position 16, e.g. a negative charged amino acid. Such modifications in some particular aspects reduce degradation that occurs through deamidation of Gln and in some embodiments, increase the activity of the glucagon analog at the GLP-1 receptor. In some aspects, the amino acid at position 20 is Glu or Lys or AIB.

Modification at Positions 21, 23, 24, and 28

In some embodiments, position 21 and/or position 24 is modified by substitution with an alpha helix promoting amino acid. In some embodiments, the alpha helix promoting amino acid forms a non-covalent intramolecular bridge with an amino acid at j–3 or i–4. In some aspects, the alpha helix promoting amino acid is AIB.

In exemplary embodiments, the amino acid at position 23 is a Ile.

In exemplary aspects, the amino acid at position 28 is an alpha, alpha, disubstituted amino acid, e.g., AIB.

Charged C-Terminus

In some embodiments, the glucagon analog is modified by amino acid substitutions and/or additions that introduce a charged amino acid into the C-terminal portion of the analog. In some embodiments, such modifications enhance stability and solubility. As used herein the term "charged amino acid" or "charged residue" refers to an amino acid that comprises a side chain that is negative-charged (i.e., de-protonated) or positive-charged (i.e., protonated) in aqueous solution at physiological pH. In some aspects, these amino acid substitutions and/or additions that introduce a charged amino acid modifications are at a position C-terminal to position 27 of SEQ ID NO: 1. In some embodiments, one, two or three (and in some instances, more than three) charged amino acids are introduced within the C-terminal portion (e.g., position(s)C-terminal to position 27). In accordance with some embodiments, the native amino acid(s) at positions 28 and/or 29 are substituted with a charged amino acids, and/or in a further embodiment one to three charged amino acids are also added to the C-terminus of the analog. In exemplary embodiments, one, two or all of the charged amino acids are negative-charged. The negative-charged amino acid in some embodiments is aspartic acid, glutamic acid, cysteic acid, homocysteic acid, or homoglutamic acid. In some aspects, these modifications increase solubility, e.g., provide at least 2-fold, 5-fold, 10-fold, 15-fold, 25-fold, 30-fold or greater solubility relative to native glucagon at a given pH between about 5.5 and 8, e.g., pH 7, when measured after 24 hours at 25° C.

C-Terminal Truncation

In accordance with some embodiments, the glucagon analogs disclosed herein are modified by truncation of the C-terminus by one or two amino acid residues. Such modified glucagon peptides, as shown herein, retain similar activity and potency at the glucagon receptor and GLP-1 receptor. In this regard, the glucagon peptides can comprise amino acids 1-27 or 1-28 of the native glucagon analog (SEQ ID NO: 1), optionally with any of the additional modifications described herein.

Charge-Neutral C-Terminus

In some embodiments, the glucagon analog comprises a modified SEQ ID NO: 1 in which the carboxylic acid of the C-terminal amino acid is replaced with a charge-neutral group, such as an amide or ester. Without being bound to any particular theory, such modifications in certain aspects increases activity of the glucagon analog at the GLP-1 receptor. Accordingly, in some embodiments, the glucagon analog is an amidated peptide, such that the C-terminal residue comprises an amide in place of the alpha carboxylate of an amino acid. As used herein a general reference to a peptide or analog is intended to encompass peptides that have a modified amino terminus, carboxy terminus, or both amino and carboxy termini. For example, an amino acid chain composing an amide group in place of the terminal carboxylic acid is intended to be encompassed by an amino acid sequence designating the standard amino acids.

Other Modifications

In some embodiments, the glucagon analogs additionally or alternatively comprise the following amino acid modifications:

(i) Substitution of Ser at position 2 with Ala;
(ii) Substitution of Tyr at position 10 with Val or Phe, or Trp;
(iii) Substitution of Lys at position 12 with Arg;
(iv) Substitution of Arg at position 17 with Gln or a small aliphatic amino acid, e.g., Ala, or a large aliphatic amino acid, e.g., Ile;
(v) Substitution of Arg at position 18 with a small aliphatic amino acid, e.g., Ala; or an imidazole-containing amino acid, e.g., His;
(vi) Substitution of Ala at position 19 with a positive-charged amino acid, e.g., Gln;
(vii) Substitution of Val at position 23 with Ile, and
(viii) Substitution of Thr at position 29 with Gly or Gln.

In some embodiments, the stability of the glucagon analog is increased by modification of the methionine at position 27, for example, by substitution with leucine or norleucine. Such modifications can reduce oxidative degradation. Stability can also be increased by modification of the Gln at position 20 or 24 or 28, e.g., by substitution with Ala, Ser, Thr, or AIB. Such modifications can reduce degradation that occurs through deamidation of Gln. Stability can be increased by modification of Asp at position 21, e.g., by substitution with another acidic residue, e.g., Glu. Such modifications can reduce degradation that occurs through dehydration of Asp to form a cyclic succinimide intermediate followed by isomerization to iso-aspartate.

In some embodiments, the glucagon analogs described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated.

Any of the modifications described herein, including, for example, the modifications which increase or decrease glucagon receptor activity and which increase GLP-1 receptor activity, can be applied individually or in combination. Combinations of the modifications that increase GLP-1 receptor activity may provide higher GLP-1 activity than any of such modifications taken alone.

Exemplary Embodiments

The present disclosures provide peptides comprising a structure similar to that of native human glucaon and exhibiting enhanced agonist activity at the GLP-1 receptor, compared to native human glucagon.

In exemplary embodiments, the peptide comprises the amino acid sequence of SEQ ID NO: 37.

In exemplary embodiments, the peptide comprises the amino acid sequence of SEQ ID NO: 13.

In exemplary embodiments, the peptide comprises the amino acid sequence of SEQ ID NO: 14.

In exemplary embodiments, the peptide comprises the amino acid sequence of SEQ ID NO: 47.

In exemplary embodiments, the peptide comprises the amino acid sequence of SEQ ID NO: 35.

In exemplary embodiments, the peptide comprises an amino acid sequence selected from the group consisting of: SEQ ID NOs: 13-16, 19-25, 27-29, and 31-33.

In exemplary embodiments, the peptide comprises an amino acid sequence selected from the group consisting of SEQ ID NOs: 26 and 30.

In exemplary embodiments, the peptide comprises an amino acid sequence selected from the group consisting of: SEQ ID NOs: 35-37.

In exemplary embodiments, the peptide comprises an amino acid sequence selected from the group consisting of: SEQ ID NOs: 38-49, and 54, and the peptide exhibits at least 100-fold selectivity for the human GLP-1 receptor versus the GIP receptor, and optionally a GLP-1 potency of at least 1%. In exemplary aspects, the peptide exhibits an EC50 at the GLP-1 receptor in accordance with the description found herein. See, for example, the teachings in the section entitled "ACTIVITY OF THE PEPTIDES AND VARIANT PEPTIDES." In exemplary aspects, the peptide exhibits agonist activity at each of the GLP-1 receptor and the glucagon receptor. In exemplary aspects, the peptide exhibits an EC50 at the glucagon receptor in accordance with the description found herein. See, for example, the teachings in the section entitled "ACTIVITY OF THE PEPTIDES AND VARIANT PEPTIDES."

In exemplary embodiments, the peptide of the present disclosures comprises an amino acid sequence selected from the group consisting of: SEQ ID NOs: 50-52, and 55, wherein the peptide exhibits at least 100-fold selectivity for the human GLP-1 receptor versus the GIP receptor, and optionally a GLP-1 potency of at least 1%. In exemplary aspects, the peptide exhibits activities as described, for example, in the section entitled "ACTIVITY OF THE PEPTIDES AND VARIANT PEPTIDES."

In exemplary embodiments, the peptide of the present disclosures comprises an amino acid sequence selected from the group consisting of: SEQ ID NOs: 38-52, 54, and 55, wherein the EC50 of the peptide at the GIP receptor is less than 100-fold (e.g., less than or about 75-fold, less than or about 50-fold, less than or about 25-fold, less than or about 20-fold, less than or about 15-fold, less than or about 10-fold, less than or about 7-fold, less than or about 5-fold, less than or about 2-fold) different from its EC50 at the GLP-1 receptor. See, for example, the teachings in the section entitled "ACTIVITY OF THE PEPTIDES AND VARIANT PEPTIDES." Optionally, the GIP potency of the peptide is within about 50-fold of the GLP-1 potency of the peptide.

In exemplary embodiments, the peptide of the present disclosures comprises an amino acid sequence of SEQ ID NO: 56. In exemplary aspects, the EC50 of the peptide at the GIP receptor is less than 100-fold (e.g., less than or about 75-fold, less than or about 50-fold, less than or about 25-fold, less than or about 20-fold, less than or about 15-fold, less than or about 10-fold, less than or about 7-fold, less than or about 5-fold, less than or about 2-fold) different from its EC50 at the GLP-1 receptor. See, for example, the teachings in the section entitled "ACTIVITY OF THE PEPTIDES AND VARIANT PEPTIDES." Optionally, the GIP potency of the peptide is within about 50-fold of the GLP-1 potency of the peptide.

In exemplary embodiments, the peptide of the present disclosures comprising an amino acid sequence of SEQ ID NO: 58.

In exemplary embodiments, the peptide of the present disclosures comprising an amino acid sequence of SEQ ID NO: 59.

In exemplary embodiments, the peptide of the present disclosures comprising an amino acid sequence of SEQ ID NO: 60.

In exemplary embodiments, the peptide of the present disclosures comprising an amino acid sequence of SEQ ID NO: 61.

In exemplary embodiments, the peptide of the present disclosures comprising an amino acid sequence of SEQ ID NO: 62. In exemplary aspects, amino acid at position 2 of SEQ ID NO: 62 is D-Ser.

In exemplary embodiments, the peptide of the present disclosures comprising an amino acid sequence of SEQ ID NO: 63.

In exemplary embodiments, the peptide of the present disclosures comprising an amino acid sequence of SEQ ID NO: 64. In exemplary aspects, amino acid at position 2 of SEQ ID NO: 64 is D-Ser.

In exemplary embodiments, the peptide of the present disclosures comprising an amino acid sequence of SEQ ID NO: 65. In exemplary aspects, amino acid at position 2 of SEQ ID NO: 65 is D-Ser.

The present disclosures further provides variant peptides comprising an amino acid sequence which is highly similar to the amino acid sequence of one of the presently disclosed peptides. In exemplary embodiments, the variant peptide of the present disclosures comprises an amino acid sequence that is at least 80%, 85%, 90% or 95% identical to amino acids 1-29 of the amino acid sequence of the peptide of any of SEQ ID NOs: 13-16, 19-33, 35-52, 54-56, wherein the variant peptide retains the activity of the parent peptide at the GLP-1 receptor, glucagon receptor, and GIP receptor (e.g., exhibits at least 100-fold selectivity for the human GLP-1 receptor versus the GIP receptor, and optionally a GLP-1 potency of at least 1%; or wherein the EC50 of the peptide at the GIP receptor is less than 100-fold different from its EC50 at the GLP-1 receptor). Optionally, the GIP potency of the variant peptide is within about 50-fold of the GLP-1 potency of the variant peptide.

In exemplary embodiments, the variant peptide of the present disclosures comprises an amino acid sequence based on an amino acid sequence of a peptide of the present disclosures but differs at one or more amino acid positions, including, but not limited to position 1, position 2, position 3, position 7, position 10, position 12, position 15, position 16, position 17, position 18, position 20, position 21, position 23, position 24, position 27, position 28, position 29. In exemplary aspects, the variant peptide may comprise a conservative substitution relative to the parent peptide, may comprise any of the amino acid modifications described herein, or may comprise an amino acid modification that returns to the amino acid present at that position in the native glucagon sequence (SEQ ID NO: 1). In exemplary aspects, the variant peptide of the present disclosures comprises an amino acid sequence based on an amino acid sequence of a peptide of the present disclosures but differs in one or more of the following ways:

a) the variant peptide comprises an acylated amino acid or an alkylated amino acid;

b) an acylated amino acid or an alkylated amino acid is replaced with the corresponding amino acid of native glucagon (SEQ ID NO: 1) at that position or a conservative substitution of the native amino acid, and optionally a new acylated or alkylated amino acid is introduced at a different position;

c) the variant peptide comprises an amino acid covalently attached to a hydrophilic moiety;

d) an amino acid covalently attached to a hydrophilic moiety is replaced with the corresponding amino acid of native glucagon (SEQ ID NO: 1) at that position, and optionally a new amino acid covalently attached to a hydrophilic moiety is introduced at a different position;

e) the C-terminal amino acid of the variant peptide comprises a C-terminal amide in place of a C-terminal alpha carboxylate;

f) an amino acid at any of positions 1 through 29 is replaced with the corresponding amino acid of native glucagon (SEQ ID NO: 1) at that position;

g) or any combinations thereof.

With regard to any of the foregoing variant peptides, in exemplary embodiments, the variant peptide comprises a hydrophilic moiety covalently attached to an amino acid at position 16, 17, 21, 24, 29, a position within a C-terminal extension, or at the C-terminus. In exemplary aspects, the variant peptide comprises a hydrophilic moiety covalently attached to an amino acid selected from the group consisting of: Cys, Lys, Orn, homocysteine, and Ac-Phe. In exemplary aspects, the hydrophilic moiety is a polyethylene glycol.

In exemplary aspects, the variant peptide comprises an acylated or alkylated amino acid, optionally, at position 10. In exemplary aspects, the variant peptide comprises an acylated or alkylated amino acid which comprises a C8 to C20 alkyl chain, a C12 to C18 alkyl chain, or a C14 or C16 alkyl chain. In exemplary aspects, the variant peptide comprises an acylated or alkylated amino acid which an acylated or alkylated amino acid of Formula I, Formula II, or Formula III, optionally, wherein the amino acid of Formula I is Lys.

In exemplary aspects, the variant peptide of the present disclosures comprises an acylated or alkylated amino acid, wherein the acyl group or alkyl group is covalently attached to the amino acid via a spacer, optionally, wherein the spacer is an amino acid or a dipeptide. In exemplary embodiments, the spacer comprises one or two acidic residues.

In any of the foregoing exemplary embodiments, the peptide or variant peptide of any of the present disclosures exhibits an (EC50 at the glucagon receptor)/(EC50 at the GLP-1 receptor) is about 20 or less (e.g., 20, 19, 18, 17, 16, 15, 14, 13, 12, 11, 10, 9, 8, 7, 6, 5, 4, 3, 2, 1, 0.5, 0.25, 0.10, 0.05, 0.025, 0.01, 0.001).

In any of the foregoing exemplary embodiments, the peptide or variant peptide of any of the present disclosures exhibits an (EC50 at the glucagon receptor)/(EC50 at the GLP-1 receptor) is more than 20 (e.g., 21, 25, 30, 40, 50, 60, 70, 80, 90, 100, 250, 500, 750, 1000, or more).

In any of the foregoing exemplary embodiments, the peptide or variant peptide of any of the present disclosures exhibits an EC50 at the GLP-1 receptor which is two- to ten-fold (e.g., 3-, 4-, 5-, 6-, 7-, 8-, 9-fold) greater than the EC50 at the glucagon receptor.

Exclusions

In exemplary embodiments, any one of the following peptides is excluded from the glucagon analogs described herein, although any of the following peptides comprising one or more further modifications thereto as described herein exhibiting the desired GLP-1 or co-agonist activity, pharmaceutical compositions, kits, and treatment methods using such compounds may be included in the invention: The peptide of SEQ ID NO: 1 with an [Arg12] substitution and with a C-terminal amide; The peptide of SEQ ID NO: 1 with [Arg12,Lys20] substitutions and with a C-terminal amide; The peptide of SEQ ID NO: 1 with [Arg12,Lys24] substitutions and with a C-terminal amide; The peptide of SEQ ID NO: 1 with [Arg12, Lys29] substitutions and with a C-terminal amide; The peptide of SEQ ID NO: 1 with a [Glu9] substitution; The peptide of SEQ ID NO: 1 missing His1, with [Glu9, Glu16, Lys29] substitutions and C-terminal amide; The peptide of SEQ ID NO: 1 with [Glu9, Glu16, Lys29] substitutions and with a C-terminal amide; The peptide of SEQ ID NO: 1 with [Lys13, Glu17] substitutions linked via lactam bridge and with a C-terminal amide; The peptide of SEQ ID NO: 1 with [Lys17, Glu21] substitutions linked via lactam bridge and with a C-terminal amide; The peptide of SEQ ID NO: 1 missing His1, with [Glu20, Lys24] substitutions linked via lactam bridge. In some embodiments, the glucagon analog is not any of the peptides disclosed in any of International Patent Application No. PCT/US2009/034448, filed on Feb. 19, 2009, and published on Aug. 26, 2010, as WO 2010/096052; International Patent Application No. PCT/US2009/068678, filed on Dec. 18, 2009, and published on Aug. 26, 2010, as WO 2010/096142; International Patent Application No. PCT/US2009/047438, filed on Jun. 16, 2009, and published on Dec. 23, 2009 as WO 2009/155258; International Patent Application No. PCT/US2008/053857, filed on Feb. 13, 2008, and published on Aug. 21, 2008, as WO 2008/101017; International Patent Application No. PCT/US2010/059724, filed on Dec. 9, 2010; International Patent Application No. PCT/US2009/047447, filed on Jun. 16, 2009, and published on Jan. 28, 2010, as WO2010/011439; International Patent Application No. PCT/US2010/38825, filed on Jun. 16, 2010, and published on Dec. 23, 2010, as WO2010/148089; International Patent Application No. PCT/US2011/022608, filed on Jan. 26, 2011; and U.S. Provisional Application No. 61/426,285, filed on Dec. 22, 2010; each of which are incorporated by reference in their entirety. In some embodiments, the glucagon analog does not include all or part of the sequence KRNRNNIA linked to the C-terminus after position 29, e.g. KRNR.

Methods of Making Peptides

The glucagon analogs of the disclosure can be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752.

Also, in the instances in which the analogs of the disclosure do not comprise any non-coded or non-natural amino acids, the glucagon analog can be recombinantly produced using a nucleic acid encoding the amino acid sequence of the analog using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N.Y., 1994.

In some embodiments, the glucagon analogs of the disclosure are isolated. In some embodiments, the glucagon analogs of the disclosure are purified. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In some embodiments, the peptides described herein are commercially synthesized by companies, such as Synpep (Dublin, Calif.), Peptide Technologies Corp. (Gaithersburg, Md.), and Multiple Peptide Systems (San Diego, Calif.). In this respect, the peptides can be synthetic, recombinant, isolated, and/or purified.

Conjugates

The invention further provides conjugates comprising one or more of the glucagon analogs described herein conjugated to a heterologous moiety. As used herein, the term "heterologous moiety" is synonymous with the term "conjugate moiety" and refers to any molecule (chemical or biochemical, naturally-occurring or non-coded) which is different from the glucagon analogs described herein. Exemplary conjugate moieties that can be linked to any of the analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising an analog of the present invention and a plasma protein, wherein the plasma protein is selected from the group consisting of albumin, transferin, fibrinogen and globulins. In some embodiments the plasma protein moiety of the conjugate is albumin or transferin. The conjugate in some embodiments comprises one or more of the glucagon analogs described herein and one or more of: a peptide (which is distinct from the glucagon and/or GLP-1 receptor active glucagon analogs described herein), a polypeptide, a nucleic acid molecule, an antibody or fragment thereof, a polymer, a quantum dot, a small molecule, a toxin, a diagnostic agent, a carbohydrate, an amino acid.

In some embodiments, the heterologous moiety is a peptide which is distinct from the glucagon and/or GLP-1 receptor active analogs described herein and the conjugate is a fusion peptide or a chimeric peptide. In some embodiments, the heterologous moiety is a peptide extension of 1-21 amino acids. In specific embodiments, the extension is attached to the C-terminus of the glucagon analog, e.g., to amino acid at position 29.

In some specific aspects, the extension is a single amino acid or dipeptide. In specific embodiments, the extension comprises an amino acid selected from the group consisting of: a charged amino acid (e.g., a negative-charged amino acid (e.g., Glu), a positive-charged amino acid), an amino acid comprising a hydrophilic moiety. In some aspects, the extension is Gly, Glu, Cys, Gly-Gly, Gly-Glu.

In some embodiments, the extension comprises an amino acid sequence of SEQ ID NO: 9 (GPSSGAPPPS), SEQ ID NO: 10 (GGPSSGAPPPS), SEQ ID NO: 8 (KRNRNNIA), or SEQ ID NO: 11 (KRNR). In specific aspects, the amino acid sequence is attached through the C-terminal amino acid of the glucagon analog, e.g., amino acid at position 29. In some embodiments, the amino acid sequence of SEQ ID NOs: 13-16 is bound to amino acid 29 of the glucagon analog through a peptide bond. In some specific embodiments, the amino acid at position 29 of the glucagon analog is a Gly and the Gly is fused to one of the amino acid sequences of SEQ ID NOs: 8-11.

In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is attached via non-covalent or covalent bonding to the analog of the present disclosure. In certain aspects, the heterologous moiety is attached to the analog of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The glucagon analog in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the analog. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

In some embodiments, the glucagon analog is conjugated to a heterologous moiety via covalent linkage between a side chain of an amino acid of the glucagon analog and the heterologous moiety. In some embodiments, the glucagon analog is conjugated to a heterologou moiety via the side chain of an amino acid at position 16, 17, 21, 24, or 29, a position within a C-terminal extension, or the C-terminal amino acid, or a combination of these positions. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety.

In some embodiments, the conjugate comprises a linker that joins the glucagon analog to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

Conjugates: Fc Fusions

As noted above, in some embodiments, the analogs are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Conjugates: Hydrophilic Moieties

The glucagon analogs described herein can be further modified to improve its solubility and stability in aqueous solutions at physiological pH, while retaining the high biological activity relative to native glucagon. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995).

In specific aspects, an amino acid residue of the analog having a thiol is modified with a hydrophilic moiety such as PEG. In some embodiments, the thiol is modified with maleimide-activated PEG in a Michael addition reaction to result in a PEGylated analog comprising the thioether linkage shown below:

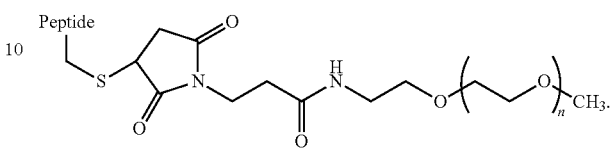

In some embodiments, the thiol is modified with a haloacetyl-activated PEG in a nucleophilic substitution reaction to result in a PEGylated analog comprising the thioether linkage shown below:

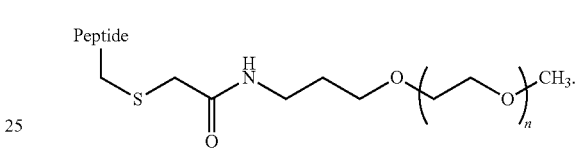

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog.

In some embodiments, the glucagon analog is conjugated to a hydrophilic moiety via covalent linkage between a side chain of an amino acid of the glucagon analog and the hydrophilic moiety. In some embodiments, the glucagon analog is conjugated to a hydrophilic moiety via the side chain of an amino acid at position 16, 17, 21, 24, or 29, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG).

Conjugates: rPEG

In some embodiments, the conjugate of the present disclosure comprises the analog having glucagon and/or GLP-1 agonist activity fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the Glucagon and/or GLP-1 agonist analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the analog of the present disclosure through a peptide bond or a proteinase cleavage site, or is inserted into the loops of the analog of the present disclosure. The rPEG in some aspects comprises an affinity tag or is linked to a PEG that is greater than 5 kDa. In some embodiments, the rPEG confers the analog of the present disclosure with an increased hydrodynamic radius, serum half-life, protease resistance, or solubility and in some aspects confers the analog with decreased immunogenicity.

Conjugates: Multimers

The invention further provides multimers or dimers of the analogs disclosed herein, including homo- or hetero-multimers or homo- or hetero-dimers. Two or more of the analogs can be linked together using standard linking agents and procedures known to those skilled in the art. For example, dimers can be formed between two peptides through the use of bifunctional thiol crosslinkers and bi-functional amine crosslinkers, particularly for the analogs that have been substituted with cysteine, lysine ornithine, homocysteine or acetyl phenylalanine residues. The dimer can be a homodimer or alternatively can be a heterodimer. In certain embodiments, the linker connecting the two (or more) analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

Pharmaceutical Compositions, Uses and Kits

Salts

In some embodiments, the glucagon analog is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or separately prepared by reacting a free base function with a suitable acid. Many of the compounds disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to, acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenyl-propionate, picrate, pivalate, propionate, succinate, tartrate, thiocyanate, phosphate, glutamate, bicarbonate, p-toluene-sulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared in situ during the final isolation and purification of the source of salicylic acid, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

Further, basic nitrogen-containing groups can be quaternized with the analog of the present disclosure as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Formulations

In accordance with some embodiments, a pharmaceutical composition is provided wherein the composition comprises a glucagon analog of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anti-caking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edetate, disodium edetate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Routes of Administration

The following discussion on routes of administration is merely provided to illustrate exemplary embodiments and should not be construed as limiting the scope in any way.

Formulations suitable for oral administration can consist of (a) liquid solutions, such as an effective amount of the analog of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the analog of the present disclosure in a flavor, usually sucrose and acacia or tragacanth, as well as pastilles comprising the analog of the present disclosure in an inert base, such as gelatin and glycerin, or sucrose and acacia, emulsions, gels, and the like containing, in addition to, such excipients as are known in the art.

The analogs of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the analog is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The analog of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind known in the art.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the analog of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the analog of the disclosure can be formulated as inclusion complexes, such as cyclodextrin inclusion complexes, or liposomes.

Dose

The analogs of the disclosure are believed to be useful in methods of treating a disease or medical condition in which glucagon receptor agonism, GLP-1 receptor agonism, or Glucagon receptor/GLP-1 receptor co-agonism plays a role. For purposes of the disclosure, the amount or dose of the analog of the present disclosure administered should be sufficient to effect, e.g., a therapeutic or prophylactic response, in the subject or animal over a reasonable time frame. For example, the dose of the analog of the present disclosure should be sufficient to stimulate cAMP secretion from cells as described herein or sufficient to decrease blood glucose levels, fat levels, food intake levels, or body weight of a mammal, in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular analog of the present disclosure and the condition of the animal (e.g., human), as well as the body weight of the animal (e.g., human) to be treated.

Many assays for determining an administered dose are known in the art. For purposes herein, an assay, which comprises comparing the extent to which blood glucose levels are lowered upon administration of a given dose of the analog of the present disclosure to a mammal among a set of mammals of which is each given a different dose of the analog, could be used to determine a starting dose to be administered to a mammal. The extent to which blood glucose levels are lowered upon administration of a certain dose can be assayed by methods known in the art, including, for instance, the methods described herein as Example 4.

The dose of the analog of the present disclosure also will be determined by the existence, nature and extent of any adverse side effects that might accompany the administration of a particular analog of the present disclosure. Typically, the attending physician will decide the dosage of the analog of the present disclosure with which to treat each individual patient, taking into consideration a variety of factors, such as age, body weight, general health, diet, sex, analog of the present disclosure to be administered, route of administration, and the severity of the condition being treated. By way of example and not intending to limit the invention, the dose of the analog of the present disclosure can be about 0.0001 to about 1 g/kg body weight of the subject being treated/day, from about 0.0001 to about 0.001 g/kg body weight/day, or about 0.01 mg to about 1 g/kg body weight/day.

In some embodiments, the pharmaceutical composition comprises any of the analogs disclosed herein at a purity level suitable for administration to a patient. In some embodiments, the analog has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprise the analog of the present disclosure at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the analog at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an analog at a concentration range of A to B mg/ml, for example, about 0.001 to about 30.0 mg/ml.

Targeted Forms

One of ordinary skill in the art will readily appreciate that the analogs of the disclosure can be modified in any number of ways, such that the therapeutic or prophylactic efficacy of the analog of the present disclosures is increased through the modification. For instance, the analog of the present disclosure can be conjugated either directly or indirectly through a linker to a targeting moiety. The practice of conjugating compounds, e.g., glucagon analogs described herein, to targeting moieties is known in the art. See, for instance, Wadhwa et al., *J Drug Targeting*, 3, 111-127 (1995) and U.S. Pat. No. 5,087, 616. The term "targeting moiety" as used herein, refers to any molecule or agent that specifically recognizes and binds to a cell-surface receptor, such that the targeting moiety directs the delivery of the analog of the present disclosures to a population of cells on which surface the receptor (the glucagon receptor, the GLP-1 receptor) is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photo-cleavable groups, acid-labile moieties, base-labile moieties and enzyme-cleavable groups. The term "linker" in some embodiments refers to any agent or molecule that bridges the analog of the present disclosures to the targeting moiety. One of ordinary skill in the art recognizes that sites on the analog of the present disclosures, which are not necessary for the function of the analog of the present disclosures, are ideal sites for attaching a linker and/or a targeting moiety, provided that the linker and/or targeting moiety, once attached to the analog of the present disclosures, do(es) not interfere with the function of the analog of the present disclosures, i.e., the ability to stimulate cAMP secretion from cells, to treat diabetes or obesity.

Controlled Release Formulations

Alternatively, the glucagon analogs described herein can be modified into a depot form, such that the manner in which the analog of the present disclosures is released into the body to which it is administered is controlled with respect to time and location within the body (see, for example, U.S. Pat. No. 4,450,150). Depot forms of analog of the present disclosures can be, for example, an implantable composition comprising the analog of the present disclosures and a porous or non-porous material, such as a polymer, wherein the analog of the present disclosures is encapsulated by or diffused throughout the material and/or degradation of the non-porous material. The depot is then implanted into the desired location within the body and the analog of the present disclosures are released from the implant at a predetermined rate.

The pharmaceutical composition in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Combinations

The glucagon analogs described herein may be administered alone or in combination with other therapeutic agents which aim to treat or prevent any of the diseases or medical conditions described herein. For example, the glucagon analogs described herein may be co-administered with (simultaneously or sequentially) an anti-diabetic or anti-obesity agent. Anti-diabetic agents known in the art or under investigation include insulin, leptin, Peptide YY (PYY), Pancreatic Peptide (PP), fibroblast growth factor 21 (FGF21), Y2Y4 receptor agonists, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARy inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to XENICAL (Orlistat) or Cetilistat (also known as ATL-962), or GT 389-255.

The peptides described herein in some embodiments are co-administered with an agent for treatment of non-alcoholic fatty liver disease or NASH. Agents used to treat non-alcoholic fatty liver disease include ursodeoxycholic acid (a.k.a., Actigall, URSO, and Ursodiol), Metformin (Glucophage), rosiglitazone (Avandia), Clofibrate, Gemfibrozil, Polymixin B, and Betaine.

The peptides described herein in some embodiments are co-administered with an agent for treatment of a neurodegenerative disease, e.g., Parkinson's Disease. Anti-Parkinson's Disease agents are furthermore known in the art and include, but not limited to, levodopa, carbidopa, anticholinergics, bromocriptine, pramipexole, and ropinirole, amantadine, and rasagiline.

In view of the foregoing, the invention further provides pharmaceutical compositions and kits additionally comprising one of these other therapeutic agents. The additional therapeutic agent may be administered simultaneously or sequentially with the analog of the present disclosure. In some aspects, the analog is administered before the additional therapeutic agent, while in other aspects, the analog is administered after the additional therapeutic agent.

Uses

It is contemplated that the glucagon analogs described herein and related pharmaceutical compositions are useful for treatment of a disease or medical condition, in which e.g., the lack of activity at the glucagon receptor, the GLP-1 receptor, or at both receptors, is a factor in the onset and/or progression of the disease or medical condition. Accordingly, the invention provides a method of treating or preventing a disease or medical condition in a patient, wherein the disease or medical condition is a disease of medical condition in which a lack of GLP-1 receptor activation and/or glucagon receptor activation is associated with the onset and/or progression of the disease of medical condition. The method comprises providing to the patient an analog in accordance with any of those described herein in an amount effective to treat or prevent the disease or medical condition.

In some embodiments, the disease or medical condition is metabolic syndrome. Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g., high fibrinogen or plasminogen activator inhibitor-1 in blood), and (6) pro-inflammatory state (e.g., elevated C-reactive protein in blood). Other risk factors may include aging, hormonal imbalance and genetic predisposition.

Metabolic Syndrome is associated with an increased risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B):66B-76B (2004)).

According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m2, or a waist measurement over 37 inches); (b) cholesterol panel showing a triglyceride level of at least 150 mg/dl or an HDL cholesterol lower than 35 mg/dl; (c) blood pressure of 140/90 or more, or on treatment for high blood pressure). (Mathur, Ruchi, "Metabolic Syndrome," ed. Shiel, Jr., William C., MedicineNet.com, May 11, 2009).

For purposes herein, if an individual meets the criteria of either or both of the criteria set forth by the 2001 National Cholesterol Education Program Adult Treatment Panel or the WHO, that individual is considered as afflicted with Metabolic Syndrome.

Without being bound to any particular theory, peptides described herein are useful for treating Metabolic Syndrome. Accordingly, the invention provides a method of preventing or treating Metabolic Syndrome, or reducing one, two, three or more risk factors thereof, in a subject, comprising providing to the subject an analog described herein in an amount effective to prevent or treat Metabolic Syndrome, or the risk factor thereof.

In some embodiments, the method treats a hyperglycemic medical condition. In certain aspects, the hyperglycemic medical condition is diabetes, diabetes mellitus type I, diabetes mellitus type II, or gestational diabetes, either insulin-dependent or non-insulin-dependent. In some aspects, the method treats the hyperglycemic medical condition by reducing one or more complications of diabetes including nephropathy, retinopathy and vascular disease.

In some aspects, the disease or medical condition is obesity. In some aspects, the obesity is drug-induced obesity. In some aspects, the method treats obesity by preventing or reducing weight gain or increasing weight loss in the patient. In some aspects, the method treats obesity by reducing appetite, decreasing food intake, lowering the levels of fat in the patient, or decreasing the rate of movement of food through the gastrointestinal system.

Because obesity is associated with the onset or progression of other diseases, the methods of treating obesity are further useful in methods of reducing complications associated with obesity including vascular disease (coronary artery disease, stroke, peripheral vascular disease, ischemia reperfusion, etc.), hypertension, onset of diabetes type II, hyperlipidemia and musculoskeletal diseases. The invention accordingly provides methods of treating or preventing these obesity-associated complications.

In some embodiments, the disease or medical condition is Nonalcoholic fatty liver disease (NAFLD). NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, the analogs described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the invention provides a method of preventing or treating Alcoholic Liver Disease, NAFLD, or any stage thereof, in a subject comprising providing to a subject an analog described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g., abnormal hepatic enzyme levels (e.g., aspartate aminotransferase AST and/or alanine aminotransferase ALT, or LDH), elevated serum ferritin, elevated serum bilirubin, and/or signs of fibrosis, e.g., elevated TGF-beta levels. In preferred embodiments, the peptides are used treat patients who have progressed beyond simple fatty liver (steatosis) and exhibit signs of inflammation or hepatitis. Such methods may result, for example, in reduction of AST and/or ALT levels.

GLP-1 and exendin-4 have been shown to have some neuroprotective effect. The invention also provides uses of the glucagon analogs described herein in treating neurodegenerative diseases, including but not limited to Alzheimer's disease, Parkinson's disease, Multiple Sclerosis, Amylotrophic Lateral Sclerosis, other demyelination related disorders, senile dementia, subcortical dementia, arteriosclerotic dementia, AIDS-associated dementia, or other dementias, a central nervous system cancer, traumatic brain injury, spinal cord injury, stroke or cerebral ischemia, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal dysmyotrophy, progressive supranuclear palsy, dystonia, muscle spasticity, tremor, retinitis pigmentosa, striatonigral degeneration, mitochondrial encephalo-myopathies, neuronal ceroid lipofuscinosis, hepatic encephalopathies, renal encephalopathies, metabolic encephalopathies, toxin-induced encephalopathies, and radiation-induced brain damage.

In some embodiments, the disease or medical condition is hypoglycemia. In some embodiments, the patient is a diabetic patient and the hypoglycemia is induced by the administration of insulin. In specific aspects, the method comprises providing the analog of the present disclosure in combination with insulin so that the analog buffers the hypoglycemic effects of the bolus administration of insulin.

In some embodiments, the glucagon analogs are used in conjunction with parenteral administration of nutrients to non-diabetic patients in a hospital setting, e.g., to patients receiving parenteral nutrition or total parenteral nutrition. Nonlimiting examples include surgery patients, patients in comas, patients with digestive tract illness, or a nonfunctional gastrointestinal tract (e.g. due to surgical removal, blockage or impaired absorptive capacity, Crohn's disease, ulcerative colitis, gastrointestinal tract obstruction, gastrointestinal tract fistula, acute pancreatitis, ischemic bowel, major gastrointestinal surgery, certain congenital gastrointestinal tract anomalies, prolonged diarrhea, or short bowel syndrome due to surgery, patients in shock, and patients undergoing healing processes often receive parenteral administration of carbohydrates along with various combinations of lipids, electrolytes, minerals, vitamins and amino acids. The glucagon analogs and the parenteral nutrition composition can be administered at the same time, at different times, before, or after each other, provided that the glucagon analog is exerting the desired biological effect at the time that the parenteral nutrition composition is being digested. For example, the parenteral nutrition may be administered, 1, 2 or 3 times per day, while the glucagon analog is administered once every other day, three times a week, two times a week, once a week, once every 2 weeks, once every 3 weeks, or once a month.

As used herein, the terms "treat," and "prevent" as well as words stemming therefrom, do not necessarily imply 100% or complete treatment or prevention. Rather, there are varying degrees of treatment or prevention of which one of ordinary skill hi the art recognizes as having a potential benefit or therapeutic effect. In this respect, the inventive methods can provide any amount of any level of treatment or prevention of a disease or medical condition in a mammal. Furthermore, the treatment or prevention provided by the method can include treatment or prevention of one or more conditions or symptoms of the disease or medical condition. For example, with regard to methods of treating obesity, the method in some embodiments, achieves a decrease in food intake by or fat levels in a patient. Also, for purposes herein, "prevention" can encompass delaying the onset of the disease, or a symptom or condition thereof.

With regard to the above methods of treatment, the patient is any host. In some embodiments, the host is a mammal. As used herein, the term "mammal" refers to any vertebrate animal of the mammalia class, including, but not limited to, any of the monotreme, marsupial, and placental taxas. In some embodiments, the mammal is one of the mammals of the order Rodentia, such as mice and hamsters, and mammals of the order Logomorpha, such as rabbits. In certain embodiments, the mammals are from the order Carnivora, including Felines (cats) and Canines (dogs). In certain embodiments, the mammals are from the order Artiodactyla, including Bovines (cows) and S wines (pigs) or of the order Perssodactyla, including Equines (horses). In some instances, the mammals are of the order Primates, Ceboids, or Simoids (monkeys) or of the order Anthropoids (humans and apes). In particular embodiments, the mammal is a human.

Kits

The glucagon analogs of the present disclosure can be provided in accordance with one embodiment as part of a kit. Accordingly, in some embodiments, a kit for administering a glucagon analog, e.g., a glucagon agonist peptide, to a patient in need thereof is provided wherein the kit comprises a glucagon analog as described herein.

In one embodiment the kit is provided with a device for administering the glucagon composition to a patient, e.g., syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the glucagon analog in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile glucagon composition is prepackaged within the syringe.

The following examples are given merely to illustrate the present invention and not in any way to limit its scope.

EXAMPLES

Example 1

Synthesis of Peptide Fragments of Glucagon

Materials:

All peptides described herein in the EXAMPLES were amidated unless specified otherwise.

MBHA resin (4-methylbenzhydrylamine polystyrene resin was used during peptide synthesis. MBHA resin, 100-180 mesh, 1% DVB cross-linked polystyrene; loading of 0.7-1.0 mmol/g), Boc-protected and Fmoc protected amino acids were purchased from Midwest Biotech. The solid phase peptide syntheses using Boc-protected amino acids were performed on an Applied Biosystem 430A Peptide Synthesizer. Fmoc protected amino acid synthesis was performed using the Applied Biosystems Model 433 Peptide Synthesizer.

Peptide Synthesis (Boc Amino Acids/HF Cleavage):

Synthesis of these analogs was performed on the Applied Biosystem Model 430A Peptide Synthesizer. Synthetic peptides were constructed by sequential addition of amino acids to a cartridge containing 2 mmol of Boc protected amino acid. Specifically, the synthesis was carried out using Boc DEPBT-activated single couplings. At the end of the coupling step, the peptidyl-resin was treated with TFA to remove the N-terminal Boc protecting group. It was washed repeatedly with DMF and this repetitive cycle was repeated for the desired number of coupling steps. After the assembly, the sidechain protection, Fmoc, was removed by 20% piperidine treatment and acylation was conducted using DIC. The peptidyl-resin at the end of the entire synthesis was dried by using DCM, and the peptide was cleaved from the resin with anhydrous HF.

For the lactamization, orthogonal protecting groups were selected for Glu and Lys (e.g., Glu(Fm), Lys(Fmoc)). After removal of the protecting groups and before HF cleavage, cyclization was performed as described previously (see, e.g., International Patent Application Publication No. WO2008/101017).

HF Treatment of the Peptidyl-Resin

The peptidyl-resin was treated with anhydrous HF, and this typically yielded approximately 350 mg (~50% yield) of a crude deprotected-peptide. Specifically, the peptidyl-resin (30 mg to 200 mg) was placed in the hydrogen fluoride (HF) reaction vessel for cleavage. 500 μL of p-cresol was added to the vessel as a carbonium ion scavenger. The vessel was attached to the HF system and submerged in the methanol/dry ice mixture. The vessel was evacuated with a vacuum pump and 10 ml of HF was distilled to the reaction vessel. This reaction mixture of the peptidyl-resin and the HF was stirred for one hour at 0° C., after which a vacuum was established and the HF was quickly evacuated (10-15 min). The vessel was removed carefully and filled with approximately 35 ml of ether to precipitate the peptide and to extract the p-cresol and small molecule organic protecting groups resulting from HF treatment. This mixture was filtered utilizing a teflon filter and repeated twice to remove all excess cresol. This filtrate was discarded. The precipitated peptide dissolves in approximately 20 ml of 10% acetic acid (aq). This filtrate, which contained the desired peptide, was collected and lyophilized.

An analytical HPLC analysis of the crude solubilized peptide was conducted under the following conditions [4.6×30 mm Xterra C8, 1.50 mL/min, 220 nm, A buffer 0.1% TFA/10% ACN, B buffer 0.1% TFA/100% ACN, gradient 5-95% B over 15 minutes]. The extract was diluted twofold with water and loaded onto a 2.2×25 cm Vydac C4 preparative reverse phase column and eluted using an acetonitrile gradient on a Waters HPLC system (A buffer of 0.1% TFA/10% ACN, B buffer of 0.1% TFA/10% CAN and a gradient of 0-100% B over 120 minutes at a flow of 15.00 ml/min. HPLC analysis of the purified peptide demonstrated greater than 95% purity and electrospray ionization mass spectral analysis was used to confirm the identity of the peptide.

Peptide Acylation

Acylated peptides were prepared as follows. Peptides were synthesized on a solid support resin using either a CS Bio 4886 Peptide Synthesizer or Applied Biosystems 430A Peptide Synthesizer. In situ neutralization chemistry was used as described by Schnolzer et al., Int. J. Peptide Protein Res. 40: 180-193 (1992). For acylated peptides, the target amino acid residue to be acylated (e.g., position ten, relative to the amino acid position numbering of SEQ ID NO: 3) was substituted with an N ε-FMOC lysine residue. Treatment of the completed N-terminally BOC protected peptide with 20% piperidine in DMF for 30 minutes removed FMOC/formyl groups. Coupling to the free ε-amino Lys residue was achieved by coupling a ten-fold molar excess of either an FMOC-protected spacer amino acid (ex. FMOC-Glu-OtBu) or acyl chain (ex. $CH_3(CH_2)_{14}$—COOH) and PyBOP or DEPBT coupling reagent in DMF/DIEA. Subsequent removal of the spacer amino acid's FMOC group is followed by repetition of coupling with an acyl chain. Final treatment with 100% TFA resulted in removal of any side chain protecting groups and the N-terminal BOC group. Peptide resins were neutralized with 5% DIEA/DMF, dried, and then cleaved from the support using HF/p-cresol, 95:5, at 0° C. for one hour. Following ether extraction, a 5% HOAc solution was used to solvate the crude peptide. A sample of the solution was then verified to contain the correct molecular weight peptide by ESI-MS. Correct peptides were purified by RP-HPLC using a linear gradient of 10% CH3CN/0.1% TFA to 0.1% TFA in 100% CH3CN. A Vydac C18 22 mm×250 mm protein column was used for the purification. Acylated peptide analogs generally completed elution by a buffer ratio of 20:80. Portions were pooled together and checked for purity on an analytical RP-HPLC. Pure fractions were lyophilized yielding white, solid peptides.

If a peptide comprised a lactam bridge and target residues to be acylated, acylation is carried out as described above upon addition of that amino acid to the peptide backbone.

Peptide PEGylation

For peptide PEGylation, 40 kDa methoxy poly(ethylene glycol) idoacetamide (NOF) was reacted with a molar equivalent of peptide in 7M Urea, 50 mM Tris-HCl buffer using the minimal amount of solvent needed to dissolve both peptide and PEG into a clear solution (generally less than 2 mL for a reaction using 2-3 mg peptide). Vigorous stirring at room temperature commenced for 4-6 hours and the reaction analyzed by analytical RP-HPLC. PEGylated products appeared distinctly from the starting material with decreased retention times. Purification was performed on a Vydac C4 column with conditions similar to those used for the initial peptide purification. Elution occurred around buffer ratios of 50:50. Fractions of pure PEGylated peptide were found and lyophilized. Yields were above 50%, varying per reaction.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 µL/min.

When the peptides were analyzed in PBS solution by ESI MS, they were first desalted using a ZipTip solid phase extraction tip containing 0.6 µL C4 resin, according to instructions provided by the manufacturer (Millipore Corporation, Billerica, Mass., see the Millipore website of the world wide web at millipore.com/catalogue.nsf/docs/C5737).

High Performance Liquid Chromatography (HPLC) Analysis:

Preliminary analyses were performed with these crude peptides to get an approximation of their relative conversion rates in Phosphate Buffered Saline (PBS) buffer (pH, 7.2) using high performance liquid chromatography (HPLC) and MALDI analysis. The crude peptide samples were dissolved in the PBS buffer at a concentration of 1 mg/ml. 1 ml of the resulting solution was stored in a 1.5 ml HPLC vial which was then sealed and incubated at 37° C. Aliquots of 100 µl were drawn out at various time intervals, cooled to room temperature and analyzed by HPLC.

The HPLC analyses were performed using a Beckman System Gold Chromatography system using a UV detector at 214 nm. HPLC analyses were performed on a 150 mm×4.6 mm C18 Vydac column. The flow rate was 1 ml/min. Solvent A contained 0.1% TFA in distilled water, and solvent B contained 0.1% TFA in 90% CH3CN. A linear gradient was employed (40% to 70% B in 15 minutes). The data were collected and analyzed using Peak Simple Chromatography software.

The initial rates of hydrolysis were used to measure the rate constant for the dissociation of the respective prodrugs. The concentrations of the prodrug and the drug were estimated from their peak areas respectively. The first order dissociation rate constants of the prodrugs were determined by plotting the logarithm of the concentration of the prodrug at various time intervals. The slope of this plot gives the rate constant I'. The half lives of the degradation of the various prodrugs were then calculated by using the formula t½=0.693/k.

Example 2

The ability of each peptide to induce cAMP was measured in a firefly luciferase-based reporter assay. The cAMP production that is induced is directly proportional to the glucagon fragment binding to the glucagon or GLP-1 receptor. HEK293 cells co-transfected with the glucagon or GLP-1 receptor, respectively, and luciferase gene linked to a cAMP responsive element were employed for the bioassay.

The cells were serum-deprived by culturing 16 hours in Dulbecco-modified Minimum Essential Medium (Invitrogen, Carlsbad, Calif.) supplemented with 0.25% Bovine Growth Serum (HyClone, Logan, Utah) and then incubated with serial dilutions of glucagon fragments for 5 hours at 37° C., 5% CO2 in 96 well poly-D-Lysine-coated "Biocoat" plates (BD Biosciences, San Jose, Calif.). At the end of the incubation, 100 µL of LucLite luminescence substrate reagent (Perkin Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). The effective 50% concentrations (EC50) were calculated by using Origin software (OriginLab, Northampton, Mass.).

Example 3

Peptides having the amino acid sequences as described in the sequence listing were made as essentially described in Example 1 and subsequently tested for in vitro agonist activity at each of the glucagon receptor and GLP-1 receptor as essentially described in Example 2. In some instances, the in vitro agonist activity at the GIP receptor was also tested. The results are shown below in Table 1.

TABLE 1

| SEQ ID NO: | Sequence | EC50 (nM) at glucagon receptor | EC50 (nM) at GLP-1 receptor | EC50 (nM) at GIP receptor |
|---|---|---|---|---|
| 13 | HaibQGTFTSDYSKYLDEKRAaibEFVC(40K-TE PEG)WLLDT-amide | 0.141 | 0.067 | no activity detected |
| 14 | HaibQGTFTSDYSKYLDERRAaibEFVC(40K-TE PEG)WLLDT-amide | 0.365 | 0.076 | 33.69 |
| 15 | HaibQGTFTSDYSKYLDEKRAaibEFVC(40K-TE PEG)WLMDT-amide | 1.102 | 0.071 | 316 |
| 16 | HaibQGTFTSDYSKYLDEKRAaibEFVC(40K-TE PEG)WLLDE-amide | 0.563 | 0.487 | 465.00 |
| 19 | HsQGTFTSDK(gammaGlu-EC16)SKYLDERAAQDFVQWLLDGRG-amide | 0.004 | 0.002 | 0.812 |
| 20 | (desNH2)HsQGTFTSDK(gammaGlu-C16)SKYLDERAAQDFVQWLLDT-amide | 0.006 | 0.004 | 1.383 |
| 21 | Ac-HsQGTFTSDK(gammaGlu-C16)SKYLDERAAQDFVQWLLDT-amide | 0.005 | 0.009 | 4.502 |
| 22 | HaibQGTFTSDK(gammaGlu-gammaGlu-C16)SKYLDaibRAAQDFVQWLMDGRG-amide | 0.005 | 0.002 | 2.372 |
| 23 | HaibQGTFTSDK(gammaGlu-gammaGlu-C16)SKYLDaibRAAQDFVQWLMKGRG-amide | 0.023 | 0.004 | 1.584 |
| 24 | HaibQGTFTSDK(gammaGlu-gammaGlu-C16)SKYLDaibRAAQDFVQWLKDGRG-amide | 0.021 | 0.004 | 1.462 |
| 25 | HaibQGTFTSDK(gammaGlu-gammaGlu-C16)SKYLDaibRAAQDFVQWLKDGRP | 0.035 | 0.003 | 2.36 |

TABLE 1-continued

| SEQ ID NO: | Sequence | EC50 (nM) at glucagon receptor | EC50 (nM) at GLP-1 receptor | EC50 (nM) at GIP receptor |
|---|---|---|---|---|
| 26 | HaibQGTFTSDK(gammaGlu-gammaGlu-C16)SKYLDaibRAAQDFVQWLKaibGRG | 0.106 | 0.004 | 3.29 |
| 27 | HsQGTFTSDK(gammaGlu-C16)SKYLDERAAQDFVQWLLKGRG-amide | 0.022 | 0.005 | 2.120 |
| 28 | HsQGTFTSDK(gammaGlu-C16)SKYLD ERAAQDFVQWLLDGRK-amide | 0.015 | 0.003 | 2.841 |
| 29 | HaibQGTFTSDK(gammaGlu-gammaGluC16)SKYLDaibRAAQDFVQWLLaibGRG-amide | 0.014 | 0.007 | 1.651 |
| 30 | HaibQGTFTSDK(gammGlu-C16)SKYLDaibRAAQDFVQWLLDGRG-amide | 0.933 | 0.0082 | 9.063 |
| 31 | HaibQGTFTSDK(gammaGlu-gammaGlu-C16)SKYLDaibRAAQDFVQWLMKGRG-acid | 0.016 | 0.007 | 2.343 |
| 32 | HaibQGTFTSDK(gammaGlu-gammaGlu-C16)SKYLDaibRAAQDFVQWLMDTKa-acid | 0.007 | 0.008 | 2.08 |
| 33 | HaibQGTFTSDK(gammaGlu-gammaGlu-C16)SKYLDaibRAAQDFVQWLMornTornE-acid | 0.023 | 0.019 | 3.959 |
| 35 | HAibQGTFTSDYSKYLDERRAAibEFVC(40K-TE PEG)WLLDGGPSSGAPPPS-amide | 1.179 | 0.085 | 16.131 |
| 36 | HaibQGTFTSDK(gammaGlu-C16)SKYLDaibRAAQDFVQWLKDGRG | 0.028 | 0.003 | 0.47 |
| 37 | HaibQGTFTSDK(gammaGlu-gammaGlu-C16)SKYLDaibRAAQDFVQWLMKTKe-acid | 0.018 | 0.016 | 3.3 |
| 38 | HaibQGTFTSDYSKYLDaibKRAaibEFVC(40K-TE PEG)WLLDT-amide | 0.141 | 0.31 | no activity detected |
| 39 | HaibQGTFTSDYSKYLDaibKRAKEFVQWLLC(40K-TE PEG)T-acid | 0.852 | 1.282 | |
| 40 | HaibQGTFTSDYSKYLDaibKRAKEFVQWLLDTC(40K-TE PEG)-amide | 1.192 | 0.653 | |
| 41 | HaibQGTFTSDYSKYLDEKRAaibEFVC(40K-TE PEG)WLLaibT-amide | 0.309 | 0.074 | no activity detected |
| 42 | HaibQGTFTSDYSKYLDEKRAaibEFVaibWLLC(40K-TE PEG)T-amide | 1.007 | 0.117 | |
| 43 | HsQGTFTSDK(gammaGlu-C16)SKYLDEQAAKEFIC(12K-ME PEG)WLLDT-amide | 0.02 | 0.011 | |
| 44 | HsQGTFTSDK(gammaGlu-C16)SKYLDEQAAKEFIC(20K-TE PEG)WLLDT-amide | 0.023 | 0.017 | |
| 45 | HaibQGTFTSDYSKYLDEKRAaibEFVC(40K-TE PEG)WLLDT-acid | 0.651 | 1.442 | no activity detected |
| 46 | HaibQGTFTSDYSKYLDaibKRAaibEFVC(40K-TE PEG)WLLDGGPSSGAPPPS-amide | 0.227 | 0.136 | no activity detected |
| 47 | HaibQGTFTSDYSKYLDEKRAaibEFVC(40K-TE PEG)WLLDGGPSSGAPPPS-amide | 0.591 | 0.052 | no activity detected |
| 48 | HsQGTFTSDK(gammaGlu-adamantylacetyl)SKYLDERAAQDFVQWLLDT-amide | 0.026 | 0.039 | |
| 49 | HsQGTFTSDK(benzoylpropionyl)SKYLDERAAQDFVQWLLDGGPSSGAPPPS-amide | 0.063 | 0.01 | |
| 51 | HaibQGTFTSDYSKYLDEKRAaibEFVC(40K-TE PEG)WLLaibGGPSSGAPPPS-amide | 2.036 | 0.062 | no activity detected |
| 52 | HaibQGTFTSDYSKYLDEKaibAKEFVC(40K-TE PEG)WLLDT-amide | 4.497 | 0.054 | no activity detected |
| 54 | HaibQGTFTSDYSKYLDEKRAaibDFVC(40K-TE PEG)WLLDT-amide | 0.939 | 0.097 | |
| 55 | HsQGTFTSDK(EDTA amide)SKYLDERAAQDFVQWLLDGGPSSGAPPPS-amide | 4.337 | 0.108 | |
| 56 | HaQGTFTSDK(gammaGlu-C16)SKYLDERAAQDFVQWLLDT-amide | 0.006 | 0.02 | 1.642 |
| 58 | HaibQGTFTSDK(C16 acyl)SKYLDSRRAaibDFVQWLMNT-amide | 0.09 | 0.025 | 35.66 |
| 59 | HaibQGTFTSDK(C16 acyl)SKYLDERRAaibDFVQWLMNT-amide | 0.051 | 0.01 | 7.477 |
| 60 | HaibQGTFTSDK(γE-C16acyl)SKYLDaibRAAQDFVQWLMKTKe-acid | 4.6 | 0.033 | 147.1 |
| 61 | HaibQGTFTSDK(γEγEC16)SKYLDERAAQDFVQWLMDT-amide | 0.009 | 0.004 | 0.676 |
| 62 | HXQGTFTSDYSKYLDEQAVRLFICWLLDGGPSSGAPPPS-amide | 0.132 | 0.006 | Not determined |

TABLE 1-continued

| SEQ ID NO: | Sequence | EC50 (nM) at glucagon receptor | EC50 (nM) at GLP-1 receptor | EC50 (nM) at GIP receptor |
|---|---|---|---|---|
| 63 | DmiaSQGTFTSDYSKYLDERRAKDFVC(CH2CONH2)WLMNT-amide | | | |
| 64 | HXQGTFTSDK(γEC16)SKYLDEQAAKEFICWLLDT-amide | 0.009 | 0.012 | 2.816 |
| 65 | HXQGTFTSDK(γEC16)SKYLDEQAAKEFICWLLDTE-amide | 0.028 | 0.024 | 47.064 |

As shown in Table 1, many if not all of the peptides exhibit enhanced activity at the GLP-1 receptor as compared to native glucagon.

Example 4

Diet induced obesity (DIO) mice are divided into groups of eight mice per group and the initial average body weight of each group is determined. Each group of mice is subcutaneously injected daily with a dose of a peptide or vehicle control for one week. The peptides of SEQ ID NOs: 12-25, 27-29, and 31-34 were tested in this study. The administered doses varied between 1 sand 10 nmol/kg for each of the peptides tested. Body weight, body composition, food intake, and blood glucose levels were determined periodically throughout the test period.

To better determine the effect of these peptides on blood glucose levels, a second experiment with db/db mice are performed. In this experiment, db/db mice are divided into groups of eight mice per group and the initial average body weight of each group is determined. Each group of mice is subcutaneously injected with a single dose of a peptide selected from the group consisting of SEQ ID NOs: 12-25, 27-29, and 31-34, wherein the dose is within the range of 3 and 30 nmole/kg. Body weight, body composition, food intake, and blood glucose levels were determined periodically throughout the test period.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide comprising or a pharmaceutically acceptable salt thereof.

2. A variant peptide comprising the amino acid sequence of the peptide of claim 1 but differs in one or more of the following ways:
   a. the variant peptide comprises an acylated amino acid or an alkylated amino acid;
   b. an acylated amino acid or an alkylated amino acid is replaced with the corresponding amino acid of native glucagon (SEQ ID NO: 1) at that position or a conservative substitution of the native amino acid, and optionally a new acylated or alkylated amino acid is introduced at a different position;
   c. the variant peptide comprises an amino acid covalently attached to a hydrophilic moiety;
   d. an amino acid covalently attached to a hydrophilic moiety is replaced with the corresponding amino acid of native glucagon (SEQ ID NO: 1) at that position, and optionally a new amino acid covalently attached to a hydrophilic moiety is introduced at a different position;
   e. the C-terminal amino acid of the variant peptide comprises a C-terminal amide in place of a C-terminal alpha carboxylate;
   f. an amino acid at any of positions 1 through 29 is replaced with the corresponding amino acid of native glucagon (SEQ ID NO: 1) at that position;
   g. or any combinations thereof;
   or a pharmaceutically acceptable salt thereof.

3. The variant peptide of claim 2, comprising (i) a hydrophilic moiety covalently attached to an amino acid at position 16, 17, 21, 24, 29, a position within a C-terminal extension, or at the C-terminus, (ii) a hydrophilic moiety covalently attached to an amino acid selected from the group consisting of: Cys, Lys, Orn, homocysteine, and Ac-Phe, (iii) or a combination thereof.

4. The variant peptide of claim 3, wherein the hydrophilic moiety is a polyethylene glycol.

5. The variant peptide of claim 3, wherein the hydrophilic moiety is a polyethylene glycol having a molecular weight of 40 kda.

6. The variant peptide of any of claim 2, comprising (i) an acylated or alkylated amino acid at position 10; (ii) an acylated or alkylated amino acid which an acylated or alkylated amino acid of Formula I, Formula II, or Formula III, optionally, wherein the amino acid of Formula I is Lys, or (iii) an acylated or alkylated amino acid, wherein the acyl group or alkyl group is covalently attached to the amino acid via a spacer, optionally, wherein the spacer is an amino acid or a dipeptide.

7. The variant peptide of claim 6, comprising an acylated or alkylated amino acid which comprises a C8 to C20 alkyl chain, a C12 to C18 alkyl chain, or a C14 or C16 alkyl chain.

8. The variant peptide of claim 6, wherein the spacer comprises one or two acidic residues.

9. The variant peptide of claim 2, wherein the (EC50 at the glucagon receptor)/(EC50 at the GLP-1 receptor) is about 20 or less.

10. The peptide variant of claim 2, wherein the (EC50) at the glucagon receptor)/(EC50 at the GLP-1 receptor) is about 20 or less.

11. A conjugate comprising a variant peptide of claim 2 conjugated to a heterologous moiety.

12. The conjugate of claim 11, wherein the heterologous moiety comprises one or more of: a peptide, a polypeptide, a nucleic acid molecule, an antibody or fragment thereof, a polymer, a quantum dot, a small molecule, a toxin, a diagnostic agent.

13. The conjugate of claim 11, comprising an extension of 1-21 amino acids C-terminal to the amino acid at position 29 or the variant peptide.

14. The conjugate of claim 13, wherein the extension is selected from the group consisting of: Gly, Glu, Cys, Gly-Gly, Gly-Glu, GPSSGAPPPS (SEQ ID NO: 9) or GGPSSGAPPPS (SEQ ID NO: 10).

15. A dimer or multimer comprising a variant peptide of claim 2.

16. A pharmaceutical composition comprising the variant peptide of claim 2, or a pharmaceutically acceptable salt thereof, and a pharmaceutically acceptable carrier.

17. A method of treating a disease or medical condition in a patient in need of treatment, wherein the disease or medical condition is selected from the group consisting of: metabolic syndrome, diabetes, obesity and liver steatosis, comprising administering to the patient the pharmaceutical composition of claim 16 in an amount effective to treat the disease or medical condition.

18. A conjugate comprising the peptide of claim 1 conjugated to a heterologous moiety.

19. The conjugate of claim 18, wherein the heterologous moiety comprises one or more of: a peptide, a polypeptide, a nucleic acid molecule, an antibody or fragment therefore, a polymer, a quantum dot, a small molecule, a toxin, or a diagnostic agent.

20. The conjugate of claim 19, comprising an extension of 1-21 amino acids C-terminal to the amino acid at position 29 of the peptide.

21. The conjugate of claim 20, wherein the extension is selected from the group consisting of: Gly, Glu, Cys, Gly-Gly, Gly-Glu, GPSSGAPPPS (SEQ ID NO: 9) or GGPSSGAPPPS (SEQ ID NO: 10).

22. A dimer or multimer comprising the peptide of claim 1.

23. A pharmaceutical composition comprising the peptide of claim 1, or a pharmaceutically acceptable salt; and a pharmaceutically acceptable carrier.

24. A method of treating a disease or medical condition in a patient in need of treatment, wherein the disease or medical condition is selected from the group consisting of: metabolic syndrome, diabetes, obesity and liver steatosis, comprising administering to the patient the pharmaceutical composition of claim 23 in an amount effective to treat the disease or medical condition.

* * * * *

UNITED STATES PATENT AND TRADEMARK OFFICE
CERTIFICATE OF CORRECTION

PATENT NO.        : 9,309,301 B2
APPLICATION NO.   : 14/127469
DATED             : April 12, 2016
INVENTOR(S)       : Dimarchi et al.

Page 1 of 1

It is certified that error appears in the above-identified patent and that said Letters Patent is hereby corrected as shown below:

In the claims

Claim 1, column 111, line 2, after "comprising," insert -- the amino acid sequence of SEQ ID NO: 14 --.

Signed and Sealed this
Fifth Day of July, 2016

Michelle K. Lee
*Director of the United States Patent and Trademark Office*